US012544579B2

(12) United States Patent
Smith et al.

(10) Patent No.: US 12,544,579 B2
(45) Date of Patent: Feb. 10, 2026

(54) HEADPIECES, IMPLANTABLE COCHLEAR STIMULATION SYSTEMS INCLUDING THE SAME AND ASSOCIATED APPARATUS AND METHODS

(71) Applicant: ADVANCED BIONICS AG, Staefa (CH)

(72) Inventors: James George Elcoate Smith, Santa Clarita, CA (US); Markus Michael Heerlein, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 645 days.

(21) Appl. No.: 17/346,343

(22) Filed: Jun. 14, 2021

(65) Prior Publication Data

US 2021/0299456 A1 Sep. 30, 2021

Related U.S. Application Data

(63) Continuation-in-part of application No. PCT/US2020/025985, filed on Mar. 31, 2020.

(51) Int. Cl.
*A61N 1/372* (2006.01)
*A61N 1/02* (2006.01)
(Continued)

(52) U.S. Cl.
CPC ..... *A61N 1/37229* (2013.01); *A61N 1/36038* (2017.08); *A61N 1/025* (2013.01)

(58) Field of Classification Search
CPC ............ A61N 1/37229; A61N 1/36038; A61N 1/025; A61N 1/0541; A61N 1/37518; A61N 1/3758
See application file for complete search history.

(56) References Cited

U.S. PATENT DOCUMENTS 4,214,366 A 7/1980 Laban
4,352,960 A 10/1982 Dormer et al.
(Continued)

FOREIGN PATENT DOCUMENTS

CN 212542072 U 2/2021
DE 202006017662 U1 9/2007
(Continued)

OTHER PUBLICATIONS

U.S. Appl. No. 17/073,322, filed Oct. 17, 2020.
(Continued)

*Primary Examiner* — Jennifer Pitrak McDonald
*Assistant Examiner* — Moussa Haddad
(74) *Attorney, Agent, or Firm* — Henricks Slavin LLP

(57) ABSTRACT

A cochlear implant headpiece in accordance with one of the present inventions includes a housing including a top wall, a bottom wall and a receptacle that extends from the top wall to the bottom wall, that defines an open top end, an open bottom end and a central axis, and that includes a receptacle lock member, a magnet apparatus defining a bottom and including a magnet and a magnet apparatus lock member, and a headpiece antenna on or within the housing. The respective configurations of the receptacle and the magnet apparatus are such that the magnet apparatus can be inserted into the receptacle and, when fully inserted into the receptacle, the magnet apparatus bottom is located within or downwardly beyond the open bottom end of the receptacle. The respective configurations of the receptacle lock member and the magnet apparatus lock member are such that the fully inserted magnet apparatus will be fixed in one of a plurality of rotational orientations around the central axis. The present inventions also include cochlear stimulation systems with a sound processor and/or a cochlear implant in combination with such a headpiece.

16 Claims, 12 Drawing Sheets

(51) Int. Cl.
*A61N 1/05* (2006.01)
*A61N 1/36* (2006.01)
*A61N 1/375* (2006.01)

(56) References Cited

U.S. PATENT DOCUMENTS 4,595,390 A 6/1986 Hakim et al.
4,606,329 A 8/1986 Hough
4,612,915 A 9/1986 Hough et al.
4,618,949 A 10/1986 Lister
RE32,947 E 6/1989 Dormer et al.
5,290,281 A 3/1994 Tschakaloff
5,755,762 A 5/1998 Bush
5,824,022 A 10/1998 Zilberman et al.
5,945,762 A 8/1999 Chen et al.
6,032,677 A 3/2000 Blechman et al.
6,178,353 B1 1/2001 Griffith et al.
6,190,305 B1 2/2001 Ball et al.
6,217,508 B1 4/2001 Ball et al.
6,227,820 B1 5/2001 Jarvik
6,292,678 B1 9/2001 Hall et al.
6,348,070 B1 2/2002 Teissl et al.
6,358,281 B1 3/2002 Berrang et al.
6,461,288 B1 10/2002 Holcomb
6,599,321 B2 7/2003 Hyde, Jr.
6,838,963 B2 1/2005 Zimmerling
7,091,806 B2 8/2006 Zimmerling et al.
7,190,247 B2 3/2007 Zimmerling
7,266,208 B2 9/2007 Charvin et al.
7,566,296 B2 7/2009 Zimmerling et al.
7,609,061 B2 10/2009 Hochmair
7,642,887 B2 1/2010 Zimmerling
7,680,525 B1 3/2010 Damadian
7,729,774 B1 6/2010 Lynch et al.
7,774,069 B2 8/2010 Olson et al.
7,856,986 B2 12/2010 Darley
7,881,800 B2 2/2011 Daly et al.
7,976,453 B2 7/2011 Zimmerling et al.
8,013,699 B2 9/2011 Zimmerling
8,027,735 B1 9/2011 Tziviskos et al.
8,118,725 B2 2/2012 Zimmerling et al.
8,255,058 B2 8/2012 Gibson et al.
8,340,774 B2 12/2012 Hochmair et al.
8,634,909 B2 1/2014 Zimmerling et al.
8,733,494 B1 5/2014 Leigh
8,734,475 B2 5/2014 Ekvall et al.
8,744,106 B2 6/2014 Ball
8,758,394 B2 6/2014 Zimmerling et al.
8,787,608 B2 7/2014 Van Himbeeck et al.
8,790,409 B2 7/2014 Van Den Heuvel et al.
8,825,171 B1 9/2014 Thenuwara et al.
8,891,795 B2 11/2014 Andersson
8,897,475 B2 11/2014 Ball et al.
RE45,701 E 9/2015 Zimmerling et al.
9,126,010 B2 9/2015 Shah et al.
9,162,054 B2 10/2015 Dalton
9,227,064 B2 1/2016 Duftner
9,295,425 B2 3/2016 Ball
9,314,625 B2 4/2016 Kasic, II et al.
9,352,149 B2 5/2016 Thenuwara et al.
RE46,057 E 7/2016 Zimmerling et al.
9,392,382 B1 7/2016 Nagl et al.
9,420,388 B2 8/2016 Ball
9,549,267 B2 1/2017 Nagl et al.
9,615,181 B2 4/2017 Nagl et al.
9,656,065 B2 5/2017 Tourrel et al.
9,919,154 B2 3/2018 Lee
9,931,501 B2 4/2018 Smyth
10,300,276 B2 5/2019 Lee et al.
10,463,849 B2 11/2019 Lee et al.
10,532,209 B2 1/2020 Lee et al.
D877,913 S * 3/2020 Lockenwitz ................. D14/230
D877,914 S * 3/2020 Lockenwitz ................. D14/230
10,646,712 B2 5/2020 Smith et al.
10,646,718 B2 5/2020 Smith et al.
10,806,936 B2 10/2020 Crawford et al.
10,821,279 B2 11/2020 Lee et al.
11,097,095 B2 8/2021 Smith et al.
11,287,495 B2 3/2022 Smith et al.
11,304,015 B2 * 4/2022 Haagerup ............. H04R 25/65
11,364,384 B2 6/2022 Smith et al.
11,471,679 B2 10/2022 Smith et al.
11,476,025 B2 10/2022 Lee et al.
11,638,823 B2 5/2023 Brehm et al.
11,752,338 B2 9/2023 Smith et al.
11,779,754 B2 10/2023 Smith et al.
11,986,656 B2 5/2024 Lee et al.
12,350,493 B2 7/2025 Smith et al.
12,364,857 B2 7/2025 Crawford et al.
2004/0012470 A1 1/2004 Zimmerling et al.
2004/0059423 A1 3/2004 Barnes et al.
2004/0063072 A1 4/2004 Honkura et al.
2004/0210103 A1 10/2004 Westerkull
2004/0260362 A1 12/2004 Darley
2005/0001703 A1 1/2005 Zimmerling
2005/0004629 A1 1/2005 Gibson et al.
2005/0062567 A1 3/2005 Zimmerling et al.
2006/0015155 A1 1/2006 Charvin et al.
2006/0116743 A1 6/2006 Gibson et al.
2006/0244560 A1 11/2006 Zimmerling et al.
2007/0053536 A1 3/2007 Westerkull
2007/0126540 A1 6/2007 Zimmerling
2008/0097496 A1 4/2008 Chang et al.
2008/0103350 A1 5/2008 Farone
2008/0192968 A1 8/2008 Ho et al.
2008/0195178 A1 8/2008 Kuzma
2008/0221641 A1 * 9/2008 Hochmair ............... A61F 11/04
607/57
2009/0048580 A1 2/2009 Gibson
2009/0099403 A1 4/2009 Zimmerling et al.
2009/0134721 A1 5/2009 Zimmerling
2009/0248155 A1 10/2009 Parker
2009/0287278 A1 11/2009 Charvin
2010/0004716 A1 1/2010 Zimmerling et al.
2010/0036458 A1 2/2010 Duftner et al.
2010/0046778 A1 2/2010 Crawford et al.
2010/0046779 A1 2/2010 Crawford et al.
2011/0009925 A1 1/2011 Leigh et al.
2011/0022120 A1 1/2011 Ball et al.
2011/0068885 A1 3/2011 Fullerton et al.
2011/0218605 A1 9/2011 Cryer
2011/0224756 A1 9/2011 Zimmerling et al.
2011/0255731 A1 10/2011 Ball
2011/0264172 A1 10/2011 Zimmerling et al.
2012/0296155 A1 11/2012 Ball
2013/0079749 A1 3/2013 Overstreet et al.
2013/0150657 A1 6/2013 Leigh et al.
2013/0184804 A1 7/2013 Dalton
2013/0281764 A1 10/2013 Bjorn et al.
2013/0343588 A1 12/2013 Karunasiri
2014/0005750 A1 1/2014 Garnham et al.
2014/0012069 A1 1/2014 Ball
2014/0012070 A1 1/2014 Nagl et al.
2014/0012071 A1 1/2014 Nagl et al.
2014/0012349 A1 1/2014 Zimmerling
2014/0121449 A1 5/2014 Kasic et al.
2014/0121586 A1 5/2014 Bertrand et al.
2014/0163692 A1 6/2014 Van den Heuvel et al.
2014/0336447 A1 11/2014 Bjorn et al.
2014/0343626 A1 11/2014 Thenuwara et al.
2015/0025613 A1 1/2015 Nyberg et al.
2015/0073205 A1 3/2015 Ball et al.
2015/0087892 A1 3/2015 Tourrel et al.
2015/0094521 A1 4/2015 Neuman et al.
2015/0100109 A1 4/2015 Feldman et al.
2015/0112407 A1 4/2015 Hartley et al.
2015/0265842 A1 9/2015 Ridler
2015/0320523 A1 11/2015 Way et al.
2015/0367126 A1 12/2015 Smyth
2015/0374989 A1 12/2015 Hazard et al.
2015/0382114 A1 12/2015 Andersson et al.
2016/0008596 A1 1/2016 Gibson et al.
2016/0023006 A1 1/2016 Ridler et al.
2016/0037273 A1 2/2016 Gustafsson

(56) References Cited

U.S. PATENT DOCUMENTS

| | | | |
|---|---|---|---|
| 2016/0144170 A1 | 5/2016 | Gibson et al. | |
| 2016/0205484 A1 | 7/2016 | Nagl et al. | |
| 2016/0213936 A1 | 7/2016 | Heerlein et al. | |
| 2016/0310737 A1 | 10/2016 | Tourrel et al. | |
| 2016/0361537 A1 | 12/2016 | Leigh et al. | |
| 2016/0381473 A1 | 12/2016 | Gustafsson | |
| 2016/0381474 A1 | 12/2016 | Gustafsson et al. | |
| 2017/0050027 A1 | 2/2017 | Andersson et al. | |
| 2017/0078808 A1 | 3/2017 | Kennes | |
| 2017/0156010 A1 | 6/2017 | Verma et al. | |
| 2017/0173334 A1 | 6/2017 | Zimmerling | |
| 2017/0239476 A1 | 8/2017 | Lee et al. | |
| 2017/0251312 A1* | 8/2017 | Crawford | A61N 1/0541 |
| 2017/0347208 A1 | 11/2017 | Jurkiewicz | |
| 2018/0028818 A1 | 2/2018 | Anderson et al. | |
| 2018/0056084 A1 | 3/2018 | Alam | |
| 2018/0110985 A1 | 4/2018 | Walter | |
| 2018/0110986 A1 | 4/2018 | Lee | |
| 2018/0133486 A1 | 5/2018 | Smith | |
| 2018/0146308 A1 | 5/2018 | Leigh et al. | |
| 2018/0160241 A1 | 6/2018 | Gustafsson et al. | |
| 2018/0160242 A1 | 6/2018 | Sriskandarajah | |
| 2018/0185634 A1 | 7/2018 | Smyth | |
| 2018/0249262 A1 | 8/2018 | Santek | |
| 2018/0270591 A1 | 9/2018 | Kennes | |
| 2018/0296826 A1 | 10/2018 | Lee et al. | |
| 2018/0303602 A1 | 10/2018 | Leigh | |
| 2018/0304078 A1 | 10/2018 | Crawford et al. | |
| 2018/0369586 A1 | 12/2018 | Lee et al. | |
| 2019/0015662 A1 | 1/2019 | Raje et al. | |
| 2019/0046797 A1 | 2/2019 | Calixto et al. | |
| 2019/0053908 A1 | 2/2019 | Cook et al. | |
| 2019/0076649 A1 | 3/2019 | Lee et al. | |
| 2019/0255316 A1 | 8/2019 | Lee et al. | |
| 2019/0298417 A1 | 10/2019 | Barrett et al. | |
| 2020/0114151 A1 | 4/2020 | Smith et al. | |
| 2020/0230422 A1 | 7/2020 | Gibson et al. | |
| 2020/0238088 A1 | 7/2020 | Smith et al. | |
| 2020/0330777 A1* | 10/2020 | Smith | A61N 1/36038 |
| 2020/0391023 A1 | 12/2020 | Lee et al. | |
| 2021/0046311 A1 | 2/2021 | Brehm et al. | |
| 2021/0106815 A1* | 4/2021 | Smith | A61N 1/37223 |
| 2021/0156934 A1 | 5/2021 | Smith et al. | |
| 2021/0316136 A1 | 10/2021 | Smith et al. | |
| 2021/0339021 A1 | 11/2021 | Brehm et al. | |
| 2022/0273948 A1 | 9/2022 | Calixto et al. | |
| 2022/0280793 A1 | 9/2022 | Smith et al. | |
| 2023/0032218 A1 | 2/2023 | Smith et al. | |
| 2023/0061335 A1 | 3/2023 | Lee et al. | |
| 2023/0115968 A1 | 4/2023 | Lee et al. | |
| 2024/0342473 A1 | 10/2024 | Smith et al. | |
| 2025/0001175 A1 | 1/2025 | Lee et al. | |
| 2025/0001186 A1 | 1/2025 | Lee et al. | |
| 2025/0050102 A1 | 2/2025 | Smith et al. | |

FOREIGN PATENT DOCUMENTS

| | | | | |
|---|---|---|---|---|
| EP | 0241307 | A2 | 10/1987 | |
| EP | 2117489 | B1 | 5/2010 | |
| EP | 2853287 | A1 | 4/2015 | |
| EP | 2560730 | B1 | 11/2016 | |
| EP | 3138605 | A1 | 3/2017 | |
| EP | 2098198 | B1 | 9/2017 | |
| EP | 3964259 | A1 | 3/2022 | |
| RU | 2727227 | C1 | 7/2020 | |
| WO | WO9858990 | A1 | 12/1998 | |
| WO | WO03081976 | A2 | 10/2003 | |
| WO | WO03092326 | A1 | 11/2003 | |
| WO | WO2004004416 | A1 | 1/2004 | |
| WO | WO2004014269 | A1 | 2/2004 | |
| WO | WO2004014270 | A1 | 2/2004 | |
| WO | WO2007024657 | A2 | 3/2007 | |
| WO | WO2009124045 | A1 | 10/2009 | |
| WO | WO2009124174 | A2 | 10/2009 | |
| WO | WO2009149069 | A2 | 12/2009 | |
| WO | WO2010000027 | A1 | 1/2010 | |
| WO | WO2010083554 | A1 | 7/2010 | |
| WO | WO2011011409 | A1 | 1/2011 | |
| WO | WO2011109486 | A2 | 9/2011 | |
| WO | WO2011133747 | A1 | 10/2011 | |
| WO | WO2012010195 | A1 | 1/2012 | |
| WO | WO2013043176 | A1 | 3/2013 | |
| WO | WO2013063355 | A1 | 5/2013 | |
| WO | WO2014011441 | A1 | 1/2014 | |
| WO | WO2014011582 | A2 | 1/2014 | |
| WO | WO2014046662 | A1 | 3/2014 | |
| WO | WO2014164023 | A1 | 10/2014 | |
| WO | WO2015065442 | A1 | 5/2015 | |
| WO | WO2016016821 | A1 | 2/2016 | |
| WO | WO2016190886 | A1 | 12/2016 | |
| WO | WO2016191429 | A1 | 12/2016 | |
| WO | WO2016207856 | A1 | 12/2016 | |
| WO | WO2017027045 | A1 | 2/2017 | |
| WO | WO2017027046 | A1 | 2/2017 | |
| WO | WO2017029615 | A1 | 2/2017 | |
| WO | WO2017034530 | A1 | 3/2017 | |
| WO | WO2017046650 | A1 | 3/2017 | |
| WO | WO2017087004 | A1 | 5/2017 | |
| WO | WO2017105510 | A1 | 6/2017 | |
| WO | WO2017105511 | A1 | 6/2017 | |
| WO | WO2017105604 | A1 | 6/2017 | |
| WO | WO2017172566 | A1 | 10/2017 | |
| WO | WO2018190813 | A1 | 10/2018 | |
| WO | WO2018191314 | A1 | 10/2018 | |
| WO | WO2018199936 | A1 | 11/2018 | |
| WO | WO2018200347 | A1 | 11/2018 | |
| WO | WO2018217187 | A1 | 11/2018 | |
| WO | WO2019027745 | A1 | 2/2019 | |
| WO | WO-2019083540 | A1 * | 5/2019 | A61N 1/36038 |
| WO | WO2019160555 | A1 | 8/2019 | |
| WO | WO2020092185 | A1 | 5/2020 | |
| WO | WO2021201845 | A1 | 10/2021 | |
| WO | WO2023063934 | A1 | 4/2023 | |
| WO | WO2023063983 | A1 | 4/2023 | |
| WO | WO2023064308 | A1 | 4/2023 | |
| WO | WO 2023113790 | A1 | 6/2023 | |
| WO | WO2024043896 | A1 | 2/2024 | |
| WO | WO2024080978 | A1 | 4/2024 | |

OTHER PUBLICATIONS

U.S. Appl. No. 17/008,291, filed Aug. 31, 2020, 20200391023 A1.
U.S. Appl. No. 16/610,502, filed Nov. 2, 2019, 20210156934 A1.
U.S. Appl. No. 16/499,311, filed Sep. 29, 2019, 20210106815 A1.
U.S. Appl. No. 16/603,868, filed Oct. 9, 2019, 20200114151 A1.
U.S. Appl. No. 16/754,126, filed Apr. 6, 2020, 20200330777 A1.
U.S. Appl. No. 17/335,161, filed Jun. 1, 2021.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
U.S. Appl. No. 17/355,225, filed Jun. 23, 2021, 20210316136 A1.
U.S. Appl. No. 17/750,352, filed May 22, 2022, 20220280793 A1.
U.S. Appl. No. 17/335,161, filed Jun. 1, 2021, 20210339021 A1.
U.S. Appl. No. 17/499,813, filed Oct. 12, 2021.
U.S. Appl. No. 17/750,352, filed May 22, 2022, 20220280793.
U.S. Appl. No. 17/335,161, filed Jun. 1, 2021, U.S. Pat. No. 20210299456 A1.
U.S. Appl. No. 17/965,580, filed Oct. 13, 2022.
U.S. Appl. No. 17/964,321, filed Oct. 12, 2022.
U.S. Appl. No. 17/680,217, filed Feb. 24, 2022.
U.S. Appl. No. 17/750,352, filed May 22, 2022.
U.S. Appl. No. 15/591,054, filed May 9, 2017, 9,919,154.
U.S. Appl. No. 17/346,161, filed Jun. 1, 2021, 20210299456 A1.
U.S. Appl. No. 17/965,580, filed Oct. 13, 2022, 20230061335 A1.
U.S. Appl. No. 16/603,868, filed Oct. 9, 2019, U.S. Pat. No. 11,364,684.
U.S. Appl. No. 18/691,947, filed Mar. 14, 2024.

(56) References Cited

OTHER PUBLICATIONS

U.S. Appl. No. 18/701,147, filed Apr. 12, 2024.
U.S. Appl. No. 18/701,199, filed Apr. 12, 2024.
U.S. Appl. No. 15/568,469, filed Oct. 21, 2017, 20180110985 A1.
U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aug. 31, 2020, U.S. Pat. No. 11,476,025.
U.S. Appl. No. 17/965,580, filed Oct. 13, 2022, U.S. Pat. No. 11,986,656.
U.S. Appl. No. 16/610,502, filed Nov. 2, 2019, U.S. Pat. No. 11,287,495.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 17/680,217, filed Feb. 24, 2022, 20220273948 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, U.S. Pat. No. 11,779,754.
U.S. Appl. No. 16/603,868, filed Oct. 9, 2019, U.S. Pat. No. 11,364,384.
U.S. Appl. No. 17/750,352, filed May 22, 2022, U.S. Pat. No. 11,752,338.
U.S. Appl. No. 16/754,126, filed Apr. 6, 2020, U.S. Pat. No. 11,471,679.
U.S. Appl. No. 17/964,321, filed Oct. 12, 2022, 20230032218 A1.
U.S. Appl. No. 17/335,161, filed Jun. 1, 2021, U.S. Pat. No. 11,638,823.
U.S. Appl. No. 17/346,343, filed Jun. 14, 2021, 20210299456 A1.
U.S. Appl. No. 18/691,947, filed Mar. 14, 2024, 20240342473 A1.
U.S. Appl. No. 18/718,442, filed Jun. 10, 2024, 20250050102 A1.
U.S. Appl. No. 18/701,147, filed Apr. 12, 2024, 20250001175 A1.
U.S. Appl. No. 17/499,813, filed Oct. 12, 2021, 20230115968 A1.
U.S. Appl. No. 18/701,199, filed Apr. 12, 2024, 20250001186 A1.
U.S. Appl. No. 18/885,649, filed Sep. 14, 2024.

* cited by examiner

HEADPIECES, IMPLANTABLE COCHLEAR STIMULATION SYSTEMS INCLUDING THE SAME AND ASSOCIATED APPARATUS AND METHODS

CROSS-REFERENCE TO RELATED APPLICATIONS

This application is a continuation-in-part of, and claims priority to, International Application No. PCT/US2020/025985, filed Mar. 31, 2020, which is incorporated herein by reference in its entirety.

BACKGROUND

1. Field

The present disclosure relates generally to implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit, a battery, and a microphone that is part of, or is in communication with, the sound processor unit. The cochlear implant communicates with the sound processor unit, and some ICS systems include a headpiece that is in communication with both the sound processor unit (e.g., a body worn processor or behind-the-ear processor) and the cochlear implant. The headpiece communicates with the cochlear implant by way of a transmitter (e.g., an antenna) on the headpiece and a receiver (e.g., an antenna) on the implant. The headpiece and the cochlear implant may include respective magnets (or respective pluralities of magnets) that are attracted to one another, thereby retaining the headpiece on the head and maintaining the position of the headpiece transmitter on the head over the implant receiver. The skin and subcutaneous tissue that separates the headpiece magnet and implant magnet is sometimes referred to as the "skin flap." In other instances, all of the external components (e.g., the battery, microphone, sound processor, antenna coil and magnet) are carried within a single headpiece. Examples of such systems are disclosed in U.S. Pat. No. 8,811,643, which is entitled "Integrated Cochlear Implant Headpiece," and U.S. Pat. No. 8,515,112, which is entitled "Modular Speech Processor Headpiece," which are incorporated herein by reference in their entireties.

One issue associated with cochlear implants is compatibility with magnetic resonance imaging ("MRI") systems. For example, the magnets in many conventional cochlear implants are disk-shaped and have north and south magnetic dipoles that are aligned in the axial direction of the disk. Such magnets produce a magnetic field that is perpendicular to the patient's skin and parallel to the axial direction, and this magnetic field direction is not aligned with, and may be perpendicular to, the direction of the MRI magnetic field (typically 1.5 Tesla or more). The misalignment of the interacting magnetic fields may result in demagnetization of the implant magnet or generate a significant amount of torque on the implant magnet that can dislodge the implant magnet and induce tissue damage.

One proposed method of accommodating an MRI magnetic field involves the use of a diametrically magnetized disk-shaped magnet that is rotatable relative to the remainder of the implant about an axis, and that has a N-S orientation which is perpendicular to the axis. U.S. Pat. No. 8,634,909 ("the '909 patent"), for example, discloses a cochlear implant system with a diametrically magnetized and rotatable disk-shaped implant magnet and a diametrically magnetized disk-shaped headpiece magnet. This type of cochlear implant is generally represented by reference numeral 10 in FIGS. 1-3. The cochlear implant 10 includes a flexible housing 12 formed from a silicone elastomer or other suitable material, a stimulation processor 14, a cochlear lead 16 with an electrode array 18, and an antenna 20 that may be used to receive data and power by way of an external antenna. A diametrically magnetized disk-shaped magnet 22 with N and S poles that is rotatable about the axis A relative to the remainder of implant 10 is positioned within the antenna portion of the housing 12. The magnet 22, which may be located within a titanium case (FIGS. 37-38), will rotate about the axis A into alignment with an MRI magnetic that is perpendicular to the axis A.

Other exemplary cochlear implants are provided with a magnet apparatus (not shown) that is better able to rotate into alignment with an MRI magnetic field than a disk-shaped magnet. Here, a plurality of elongate diametrically magnetized magnet are positioned within a frame. The frame and magnets are located within a magnet case. The frame is rotatable relative to the case about the central axis of the case, and the magnets are rotatable relative to the frame about respective axes that are either perpendicular to the central axis or slightly non-perpendicular to the central axis. The magnets align with one another in the N-S direction in the absence of a relatively strong external magnetic field (e.g., an MRI magnetic field), and the at rest N-S orientation of the magnets will be perpendicular to the central axis. Various examples of such magnet apparatus are disclosed in U.S. Pat. No. 10,463,849, which is incorporated herein by reference in its entirety.

The cochlear implant 10 (or cochlear implants with the magnet apparatus described in the preceding paragraph) may be used in conjunction with a headpiece 30 that includes a housing 32 in which components, such as a printed circuit board (not shown) that carries an antenna 34 and other electronic components, are located. An electrical connector 36 connects the circuit board to a sound processor (e.g., a BTE sound processor) by way of a cable 38. A diametrically magnetized disk-shaped magnet 40 is also provided. The magnetic attraction between the magnets 22 and 40 maintains the position of the headpiece 30 against the skin flap over the cochlear implant 10, and causes the N and S poles of the rotatable implant magnet 22 to align with the S and N poles of the headpiece magnet 40 in the manner shown (or the S and N poles of the magnets in the above-described magnet apparatus). The '909 patent indicates that the headpiece magnet may either be fixed within the headpiece to prevent its rotation, or allowed to rotate on its axis like the implant magnet.

The present inventors have determined that there are a number of issues associated with the above-described cochlear implant systems. For example, the proper retention of the headpiece 30 depends on the normal retention force NRF and the lateral retention force LRF (FIG. 3). The normal retention force NRF is a function of the strength of the diametrically magnetized implant and headpiece magnets 22 and 40 (or multi-magnet magnet apparatus) as well as the distance between the implant and headpiece magnets, while the lateral retention force LRF is a function of the normal retention force NRF and the coefficient of friction between the headpiece and the associated head surface. Pressure on the skin flap can result in discomfort and tissue necrosis when the normal retention force NRF is too high, while the headpiece will not be retained when the normal retention force NRF is too low. Additionally, the normal retention force NRF is maximized when the N and S poles of the implant and headpiece magnets are aligned N to S and S to N and, for a given normal retention force NRF, the lateral retention force LRF is maximized when the N-S direction (or "axis") of the magnets is aligned with the gravitational direction G.

Given that headpieces are typically worn with the headpiece cable extending downwardly in the gravitational direction G (FIG. 3), some conventional headpieces fixedly align the N-S direction of the headpiece magnet with the headpiece cable, thereby typically aligning the N-S direction of the headpiece magnet with the gravitational direction G. The present inventors have determined is can be problematic for persons who do not wear their headpiece in the typical manner and instead wear the headpiece in, for example, the manner illustrated in FIG. 4. Although the strength of the headpiece magnet 44 will cause the rotatable implant magnet 22 (FIG. 3) to rotate into N-S alignment with the headpiece magnet, the N-S direction of the magnets will not be aligned with the gravitational direction G due to the fixed orientation of the headpiece magnet. Such misalignment results in a less than optimal lateral retention force LRF for a given normal retention force NRF.

The present inventors have also determined that there are many instances where is it difficult to achieve sufficient normal retention force NRF due to, for example, relatively thick patient skin flaps. Given that the magnetic attraction between two magnets is inversely proportional to the square of the distance between the magnets, small changes in the distance between the implant and headpiece magnets can result in a relatively large reduction in the normal retention force NRF and, by extension, the lateral retention force LRF.

The present inventors have also determined that there may be instances where it is necessary or desirable to ascertain information about the magnet or magnet apparatus that is included in a patient's implanted cochlear implant. Such information may include, for example, precise location, type of magnet apparatus, overall shape, magnet configuration, polar orientation and/or pole location. For example, a clinician performing a headpiece fitting may not know the polar orientation of magnet is included in a patient's implanted cochlear implant (e.g., an axially magnetized magnet or a diametrically magnetized magnet), or may simply prefer to confirm the available information about a magnet apparatus, so that the proper headpiece magnet can be more easily identified. Information about the magnet or magnet apparatus is also useful in surgical and diagnostic settings. For example, information concerning the magnet or magnet apparatus allows MRI technicians to determine whether or not head bandaging is required, while surgeons would benefit from knowing the exact position of the magnet or magnet apparatus, as well as the associated antenna, during revision surgery, magnet retrofit surgery, and active insertion monitoring. Position information is also useful to barbers, hairdressers and others who remove hair over the region of the magnet or magnet apparatus for comfort and retention purposes. Magnet or magnet apparatus position information is also useful to cochlear implant recipients, as well as the parents or other caregivers of young recipients, during the initial training period, especially in the case of bi-lateral patients whose implants may be in different locations relative to the pinna.

SUMMARY

A cochlear implant headpiece in accordance with one of the present inventions comprises a housing including a top wall, a bottom wall and a receptacle that extends from the top wall to the bottom wall, that defines an open top end, an open bottom end and a central axis, and that includes a receptacle lock member, a magnet apparatus defining a bottom and including a magnet and a magnet apparatus lock member, and a headpiece antenna on or within the housing. The respective configurations of the receptacle and the magnet apparatus are such that the magnet apparatus can be inserted into the receptacle and, when fully inserted into the receptacle, the magnet apparatus bottom is located within or downwardly beyond the open bottom end of the receptacle. The respective configurations of the receptacle lock member and the magnet apparatus lock member are such that the fully inserted magnet apparatus will be fixed in one of a plurality of rotational orientations around the central axis. The present inventions also include cochlear stimulation systems with a sound processor and/or a cochlear implant in combination with such a headpiece.

A headpiece fitting kit in accordance with one of the present inventions comprises a plurality of magnet apparatus, each magnet apparatus including a magnet and a magnet apparatus lock member and defining a bottom and a respective magnet apparatus strength. Each magnet apparatus is configured for use with a cochlear implant headpiece housing including a top wall, a bottom wall and a receptacle that extends from the top wall to the bottom wall, that defines an open top end, an open bottom end and a central axis, and that includes a receptacle lock member. The respective configurations of the receptacle and each magnet apparatus are such that any one of the magnet apparatus can be inserted into the receptacle and, when fully inserted into the receptacle, the bottom of the inserted magnet apparatus is located within or downwardly beyond the open bottom end of the receptacle. The respective configurations of the receptacle lock member and the magnet apparatus lock member of each magnet apparatus are such that the fully inserted magnet apparatus will be fixed in one of a plurality of rotational orientations around the central axis. At least two of the magnet apparatus have different magnet apparatus strengths.

There are a variety of advantages associated with such headpieces, systems and kits. By way of example, but not limitation, the N-S orientation of the headpiece magnet relative to the remainder of the headpiece may be adjusted, while reducing the distance between the headpiece magnet and the implanted cochlear implant magnet, thereby increasing in the magnetic attraction between the magnets, as compared to that achieved with conventional headpieces. The kits may include a plurality magnet apparats having different strengths to be tried during the fitting process.

A method in accordance with one of the present inventions includes the step of placing a magnetic viewing device on a patient's head over an implanted cochlear implant that includes a magnet or a magnet apparatus. The image displayed by the magnetic viewing device is indicative of one or more of location, type of magnet apparatus, overall shape, magnet configuration, polar orientation and/or pole location thereby allowing a clinician, surgeon, MRI technician or other person to identify the magnet or magnet apparatus that is implanted in the patient as well as the location of the magnet or magnet apparatus.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

Figure 1:
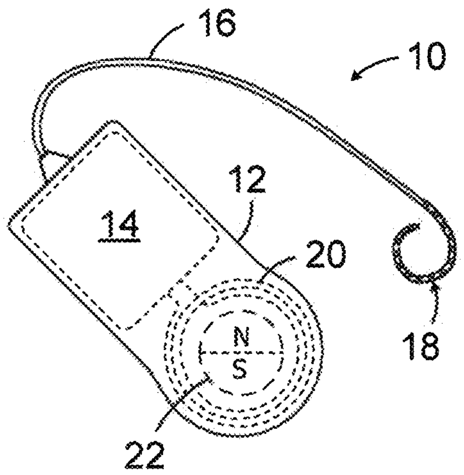
FIG. 1 Prior Art
FIG. 1 is a plan view of a conventional cochlear implant.
Figure 2:
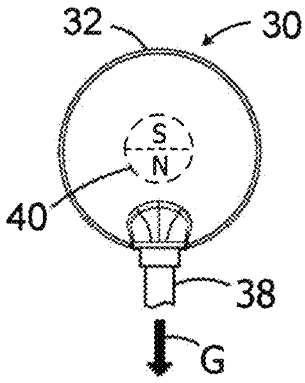
FIG. 2 Prior Art
FIG. 2 is a plan view of a conventional headpiece.
Figure 3:
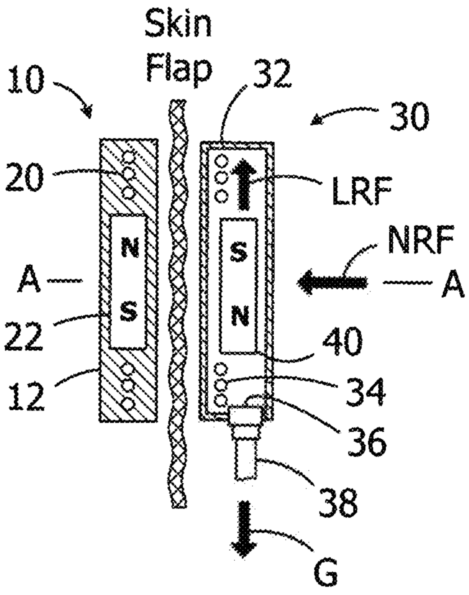
FIG. 3 Prior Art
FIG. 3 is a simplified side, section view of a cochlear implant and the headpiece illustrated in FIGS. 1 and 2.
Figure 4:
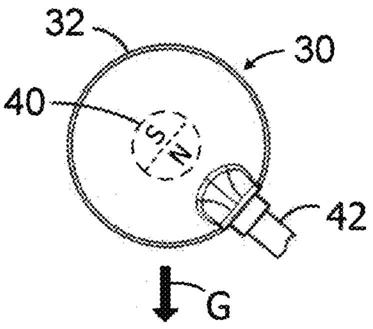
FIG. 4 Prior Art
FIG. 4 is a plan view of the headpiece illustrated in FIG. 2.
Figure 5:
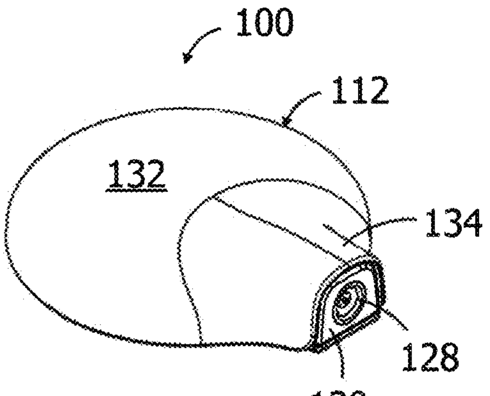
FIG. 5 is a perspective view of a headpiece in accordance with one embodiment of a present invention.

The following is a detailed description of the best presently known modes of carrying out the inventions. This description is not to be taken in a limiting sense, but is made merely for the purpose of illustrating the general principles of the inventions.

An exemplary headpiece in accordance with at least one of the present inventions is illustrated in FIGS. 5-9 and is generally represented by reference numeral 100. The exemplary headpiece 100 may include a housing 102, with a base member 104 and a dome-like member 106 that together define a ring-like portion 108 and a projection 110, and a removable cap 112 that may be secured to the housing. A removable diametrically magnetized headpiece magnet apparatus (or "magnet apparatus") 114 is located within a receptacle 116 that extends through the housing 102. As is discussed in greater detail below, the magnet apparatus 114 may be fixed at any one of a plurality of rotational orientations located around a central axis A (of both the magnet apparatus 114 and the receptacle 116) to obtain the desired N-S direction of the magnet apparatus relative to the housing 102. The magnet apparatus 114 may also be removed and replaced with another magnet apparatus having different properties such as, for example, greater magnetic strength.

Figure 46:
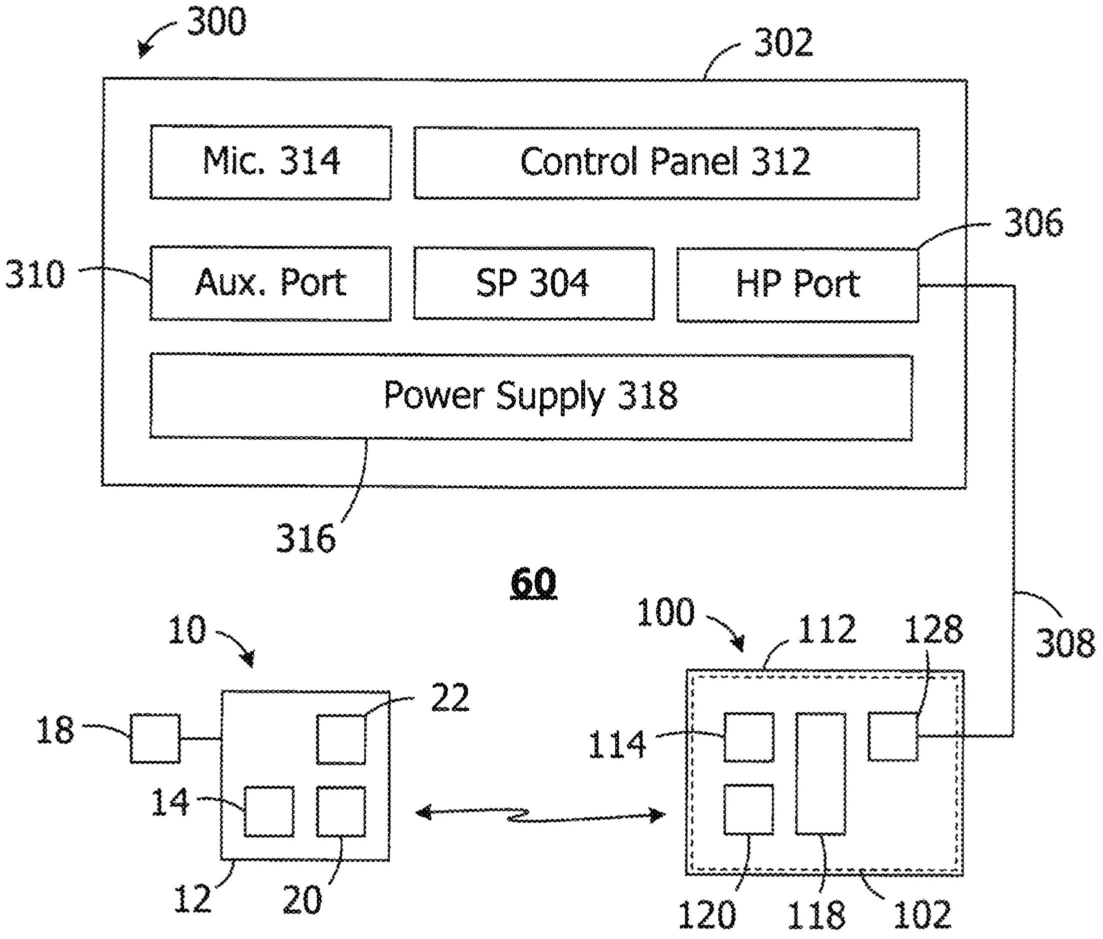
FIG. 46 is a block diagram of an ICS system in accordance with one embodiment of a present invention.

An annular printed circuit board (PCB) 118 that carries various headpiece electronic components on the top side thereof is located within the housing ring-like portion 108. An antenna may be may be located on, located within, or otherwise carried by the housing 102. In the illustrated embodiment, an antenna 120 is located on the bottom side of the PCB 118 and the PCB is positioned on the top (or "interior") surface 122 of the base member 104. In other implementations, the antenna may be carried by the base member 104. In the illustrated embodiment, the PCB 118 and antenna 120 are hermetically sealed within the housing, and the dome-like member 106 may be secured to the base member 104 through the use of ultrasonic welding, adhesive, or any other suitable instrumentality. The bottom (or "exterior") surface 124 of the base member 104 may be concave or flat, and may include a plurality of protrusions 126. A connector 128, such as a RF connector, is connected to the PCB 118 and extends through an end wall 130 on the housing projection 110. The connector 128 may be used to connect the PCB 118 to a sound processor (e.g., a BTE sound processor) by way of a cable 308 (FIG. 46). The exemplary cap 112 has a main portion 132 that covers the magnet apparatus 114 and receptacle 116, and a hood 134 that covers the projection 110. The housing 102 and cap 112 may be attached to one another with any suitable instrumentality. In the illustrated implementation, the housing 102 includes a plurality of latch indentations 136 that are engaged by a corresponding plurality of latches 138 on the cap 112 when the cap is positioned over the housing 102 in the manner illustrated in FIG. 5.

Figure 6:
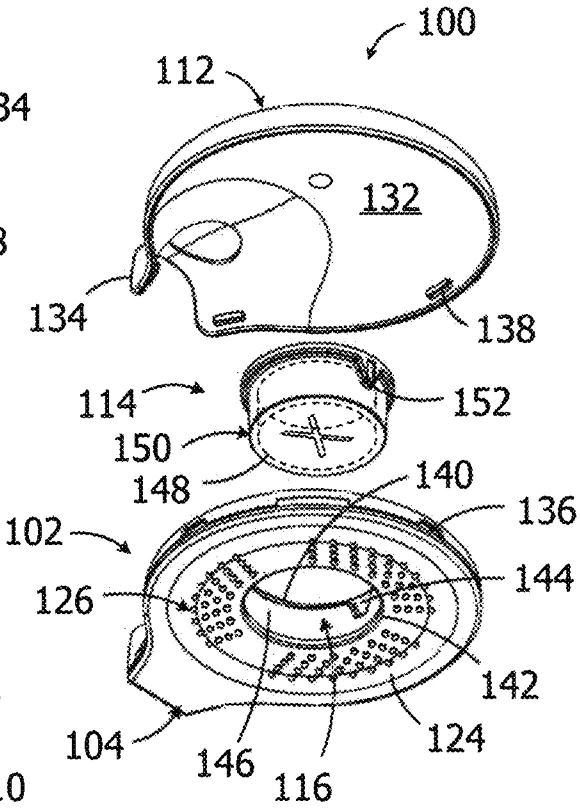
FIG. 6 is an exploded perspective view of the headpiece illustrated in FIG. 5.
Figure 7:
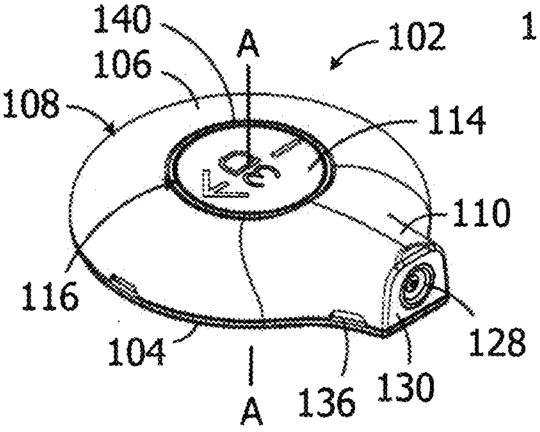
FIG. 7 is a perspective view of a portion of the headpiece illustrated in FIG. 5.
Figure 8:
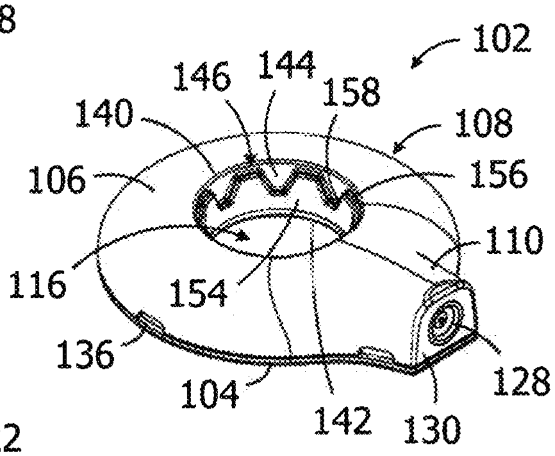
FIG. 8 is a perspective view of a portion of the headpiece illustrated in FIG. 5.
Figure 9:
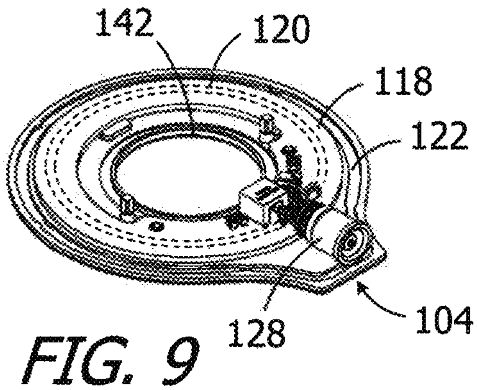
FIG. 9 is a perspective view of a portion of the headpiece illustrated in FIG. 5.
Figure 10:
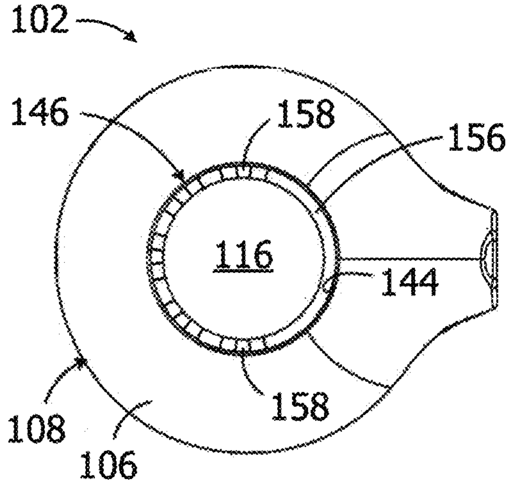
FIG. 10 is a plan view of a portion of the headpiece illustrated in FIG. 5.
Figure 11:
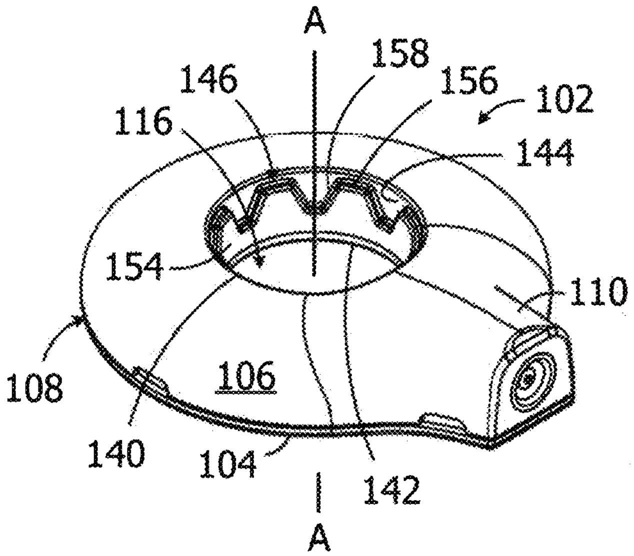
FIG. 11 is a perspective view of a portion of the headpiece illustrated in FIG. 5.

Referring more specifically to FIGS. 6-8, the exemplary receptacle 116 extends completely through the housing 102, has an open top end 140 and an open bottom end 142, and includes a cylindrical wall 144 and a lock member 146 on the cylindrical wall. It should be noted here that, in the context of the present application, words such as "bottom" and "downwardly" are used to describe structures that are adjacent to or that face the wearer's head when the headpiece is in use, while words such as "top" and "upwardly" are used to describe structures that are not adjacent to or that face away from the wearer's head when the headpiece is in use. The exemplary magnet apparatus 114 includes a diametrically magnetized magnet 148 (FIG. 6) that is located within a magnet case 150. A lock member 152 is located on, and projects outwardly from, the outer surface of the magnet case 150. The lock members 146 and 152 cooperate with one another to fix the rotational orientation of the magnet apparatus 114 relative to the housing 102 to the orientation that provides the desired N-S direction of the magnet apparatus relative to the housing. To that end, and turning to FIGS. 10 and 11, the exemplary lock member 146 includes a base 154 that defines a top surface 156 and a plurality of indentations 158 extending downwardly from the top surface. There are five indentations 158 in the illustrated embodiment. Two of the indentations 158 are angularly offset from one another by 180 degrees around the axis A, and the remaining three indentations are located between the two that are offset by 180 degrees. The indentations 158, which may be V-shaped (as shown) or any other suitable shape, are also equidistant (45 degrees) from one another in the illustrated implementation.

Figure 12:
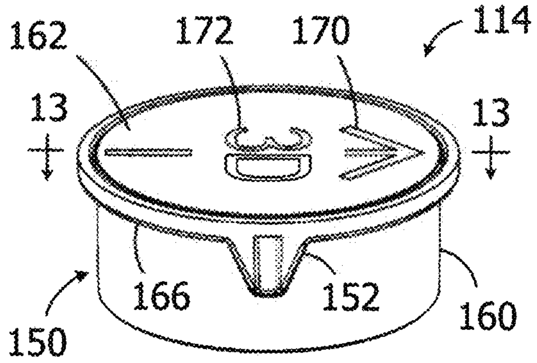
FIG. 12 is a perspective view of the magnet apparatus in the headpiece illustrated in FIG. 5.
Figure 13:
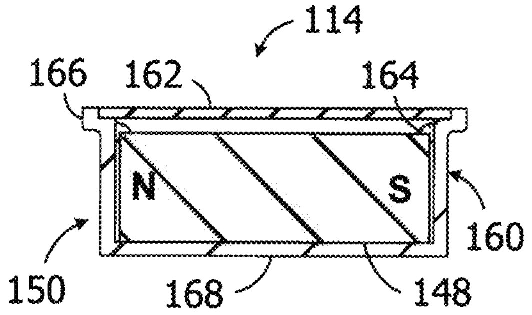
FIG. 13 is a section view taken along line 13-13 in FIG. 12.

As illustrated in FIGS. 12 and 13, the magnet case 150 of the exemplary magnet apparatus 114 includes a cylindrical container 160 that is configured to receive the diametrically magnetized magnet 148 and a cover 162 that prevents removal of the magnet from the magnet case. The cover 162 may also be used to hermetically seal the magnet 148 within the container 160. The cover 162 may be secured to the container 160 through the use of ultrasonic welding, adhesive, or any other suitable instrumentality. In other implementations, the magnet case may be a one-piece structure in which the magnet is molded. The magnet 148 may in some instances also be secured in container 160 with adhesive 164. The container 160 is sized and shaped such that it can be placed into the receptacle 116. A flange 166 is provided at the top end of the container 160, and the lock member 152 extends downwardly from the flange. The magnet apparatus flange 166 extends radially outward from the container 160. The flange 166 also rests on the lock member top surface 156 when the magnet apparatus is fully inserted to receptacle 116 and, as can be seen in FIG. 7, the respective sizes of the magnet apparatus 114 and the receptacle 116 result in the top surfaces of the cover 162 and the flange 166 being flush with the adjacent top surface of the housing annular portion 108.

As is discussed in greater detail below with reference to FIG. 18, the respective configurations of the magnet apparatus 114 and the receptacle 116 result in the container bottom wall 168 extending to or through the open bottom end 142 of the receptacle 116, and this is the same regardless of which indentation 158 the lock member 152 is located within. Put another way, the position of the magnet apparatus 114 along the central axis A is the same regardless of the rotational orientation of magnet apparatus 114 around the central axis A. As a result, the distance between the headpiece magnet 148 and the implant magnet are decreased, and the attraction force between the magnets is correspondingly increased, as compared to an arrangement where the bottom wall of the magnet apparatus container rests on top (or "inner") surface of the headpiece bottom wall.

The lock member 152 is configured to fit into the indentations 158. In the illustrated implementation, the lock member 152 is V-shaped. Other suitable magnet apparatus lock member configurations, which correspond to other housing lock member configurations, may be employed. By way of example, but not limitation, the magnet apparatus lock member and the housing indentations may be rectangular or semi-circular. Alternatively, or in addition, the magnet apparatus lock member may be in the form of an indentation that extends upwardly from the container bottom wall 168, while the housing lock member may include corresponding projections in place of the illustrated indentations.

It should also be noted that the lock member 152 and/or the flange 166 may cooperate with the lock member 146 to prevent the magnet apparatus 114 from exiting the housing 102 by way of the open bottom end 142 of the receptacle 116. In the illustrated embodiment, once the magnet apparatus 114 is fully inserted into the receptacle 116, the lock member 152 will be unable to pass the associated indentation 158, and the flange 166 (which has a diameter greater than that of the lock member 146) will abut the base top surface 156, thereby preventing further downward movement.

Figure 14:
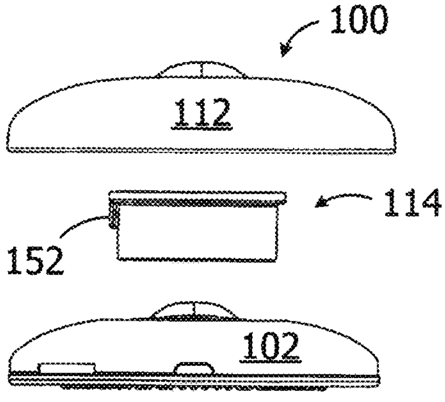
FIG. 14 is an exploded end view of the headpiece illustrated in FIG. 5.
Figure 15:
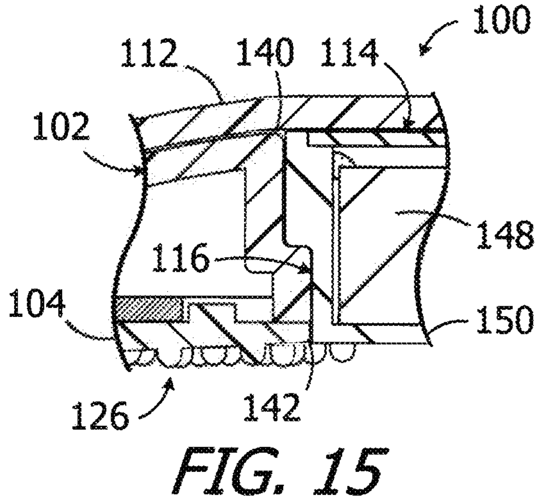
FIG. 15 is a section view of a portion of the headpiece illustrated in FIG. 5.

The removable cap 112 prevents the magnet apparatus 114 from exiting the housing 102 by way of the open top end 140 of the receptacle 116. Referring to FIGS. 14 and 15, the magnet apparatus 114 may be placed into the receptacle 116 in the desired N-S orientation while the cap 112 is disconnected from the housing 102. The cap 112 may then be placed onto the housing 102 and secured thereto with, for example, the illustrated indentations 136 and latches 138 (FIG. 6) to maintain the desired N-S orientation and hold the magnet apparatus 114 within the receptacle 166.

The magnet apparatus 114 may also include visible and/or tactile indicia (or some other instrumentality) which identifies the N-S direction of the diametrically magnetized magnet 148 and, in some instances, provides other information about the magnet apparatus 114. Such information allows the user to, for example, position the magnet apparatus 114 within the receptacle 116 in the desired N-S orientation. The exemplary magnet apparatus 114 includes indicia on the cover 162 in the form of an arrow 170 that identifies the N-S direction and one or more alpha and/or numeric elements 172 which indicate the type of magnet (i.e., diametrically magnetized or axially magnetized) that is located within the magnet case 150, as is shown in FIG. 12. Such information may be combined into a single indicia type that provides more than one type of information. For example, an arrow could be used to represent that the magnet is a diametrically magnetized magnet as well as the N-S direction of the magnet. Another example involves the use of one or more chevrons. Here, the orientation of the chevrons may be used to identify the N-S direction of the magnet, while the number of chevrons may be used to indicate the strength of the magnet apparatus. Color, such the color of the container 160 and/or cover 162, may also be employed. Other indicia may be used to identify the magnetic strength of a magnet apparatus, as is discussed below with reference to FIGS. 19A-22B.

Figure 16A:
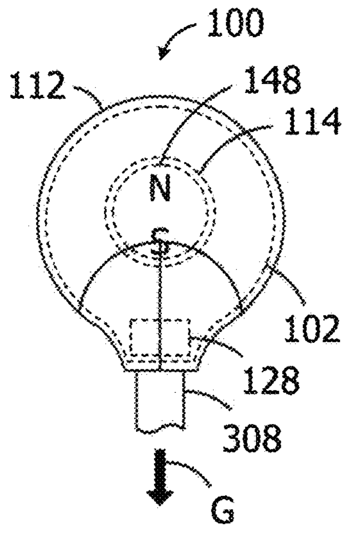
FIG. 16A-16C are plan views of the headpiece illustrated in FIG. 5 with the magnet apparatus in a single orientation and the remainder of the headpiece in various orientations.
Figure 16B:
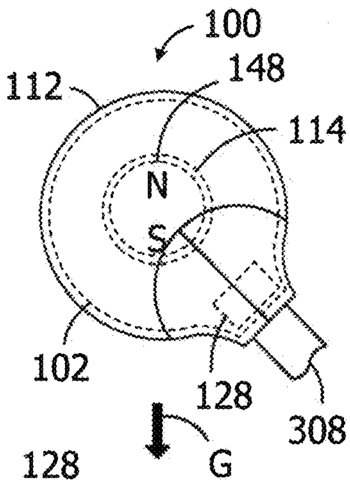
Figure 16C:
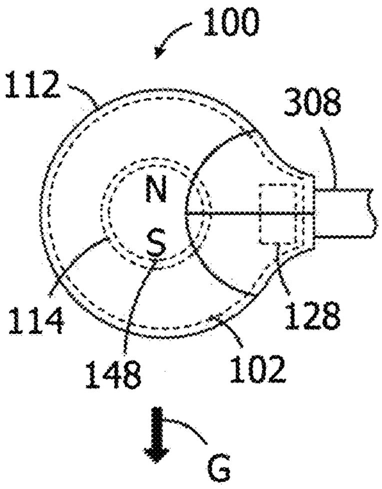
Figure 17A:
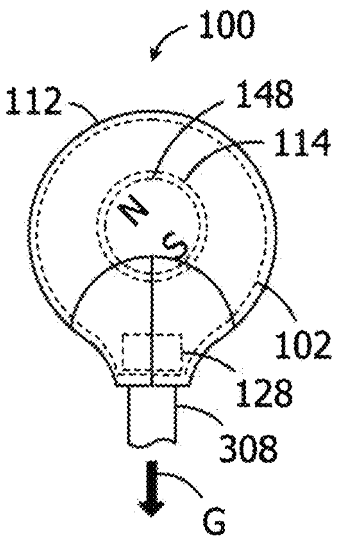
FIG. 17A-17C are plan views of the headpiece illustrated in FIG. 5 with the magnet apparatus and the remainder of the headpiece in various orientations.
Figure 17B:
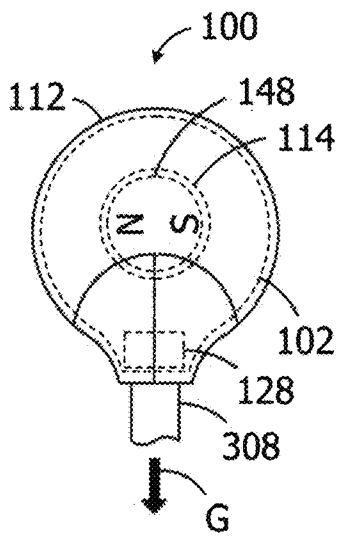
Figure 17C:
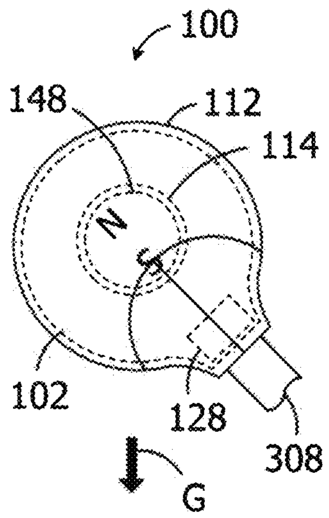

The present headpiece 100 (as well as the other headpieces described herein) may be arranged one the wearer's head in a variety of orientations while, at the same time, the magnet apparatus 114 (as well as the other magnet apparatus described herein) may be oriented in such a manner that the N-S direction of the magnet is aligned with the gravitation direction or, if so desired, the N-S direction of the magnet is not aligned with the gravitation direction. For example, as illustrated in FIGS. 16A-16C, the headpiece 100 may be oriented in such a manner that the lateral retention force is maximized for a particular magnet strength. The headpiece 100 may oriented such that the connector 128 faces in the gravitational direction G and the cable 308 extends in the gravitational direction G (FIG. 16A), or such that the connector 128 faces in a direction that is offset from the gravitational direction G by 45 degrees and the cable 308 extends in a direction that is offset from the gravitational direction G by 45 degrees (FIG. 16B), or such that the connector 128 faces in a direction that is offset from the gravitational direction G by 90 degrees and the cable 308 extends in a direction that is offset from the gravitational direction G by 90 degrees (FIG. 16C). In each instance, the magnet apparatus 114 is fixed within the housing 102 in an orientation that results in the N-S direction of the diametrically magnetized magnet 148 being the gravitational direction G, thereby maximizing the lateral retention force. In other instances, the lateral retention force may be reduced by orienting the magnet apparatus 114 within the housing 102 in such a manner that N-S direction of the diametrically magnetized magnet 148 is in a direction other than the gravitational direction G. For example, the headpiece 100 may oriented such that the connector 128 faces in the gravitational direction G and the cable 308 extends in the gravitational direction G, while the magnet apparatus 114 is oriented within the housing 102 in such a manner that N-S direction of the diametrically magnetized magnet 148 is offset from the gravitational direction G by 45 degrees (FIG. 17A) or by 90 degrees (FIG. 17B). The headpiece 100 may also be oriented such that the connector 128 faces in a direction that is offset from the gravitational direction G by 45 degrees and the cable 308 extends in a direction that is offset from the gravitational direction G by 45 degrees, while the magnet apparatus 114 is oriented within the housing 102 in such a manner that N-S direction of the diametrically magnetized magnet 148 is also offset from the gravitational direction G by 45 degrees (FIG. 17C).

Figure 18:
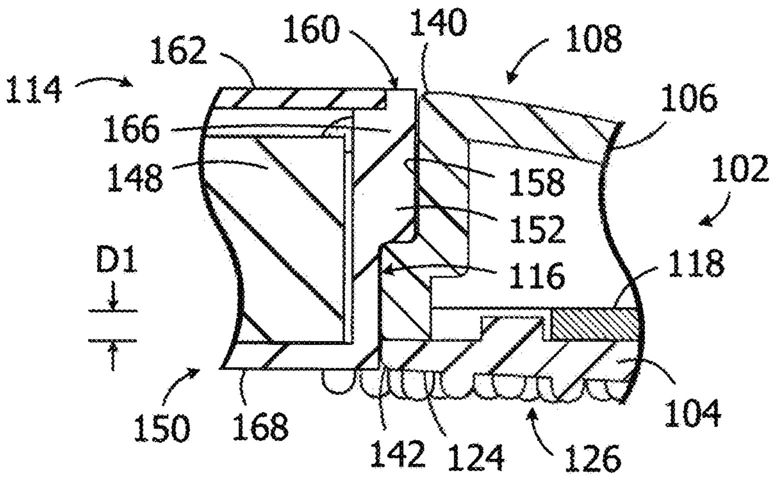
FIG. 18 is a section view of a portion of the headpiece illustrated in FIG. 5.

Turning to FIG. 18, and as alluded to above, when the magnet apparatus 114 is fully inserted into the receptacle 116 in the exemplary implementation, with the lock member 152 in one of the lock member indentations 158, the case bottom wall 168 extends through the housing base member 104 to the receptacle open bottom end 142. In this instance, the bottom end of the case 150 is aligned with the adjacent portion of the bottom surface 124 of the base member 104. As compared to an otherwise identical headpiece where the receptacle does not extend though the bottom wall of the housing (because the bottom end is not open) and the bottom wall of the magnet apparatus container rests on the inner surface of the headpiece bottom wall, the distance between the present headpiece magnet 148 and the implanted cochlear implant magnet (not shown) will be decreased by a distance D1. The distance D1 is equal to the thickness of the base member 104 in the illustrated embodiment. Because the magnetic attraction between two magnets is inversely proportional to the square of the distance between the magnets, the percent increase in the magnetic attraction is relatively large even when distance D1 is a small distance. Assuming for example that a magnet-to-magnet distance of 6.0 mm is decreased by 0.6 mm, the magnetic attraction will be 12% greater.

Magnet apparatus with different magnetic strengths may be used in conjunction with the same headpiece housing 102. In the illustrated implementation, where the magnets within the magnet apparatus are formed from the same magnetic material (e.g., N55 grade neodymium) and the case bottom wall 168 always faces the implant magnet, the size of a magnet and the distance of the magnet from the case bottom wall will be determinative of magnet apparatus strength. Each magnet apparatus may be provided with indicia (or another suitable instrumentality) that allows the user to discern the relative magnetic strength of that magnet apparatus.

Figure 19A:
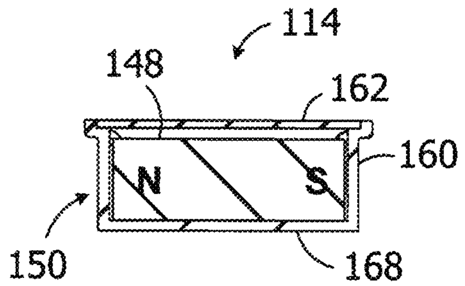
FIGS. 19A and 19B are section and bottom views of the magnet apparatus of the headpiece illustrated in FIG. 5.
Figure 19B:
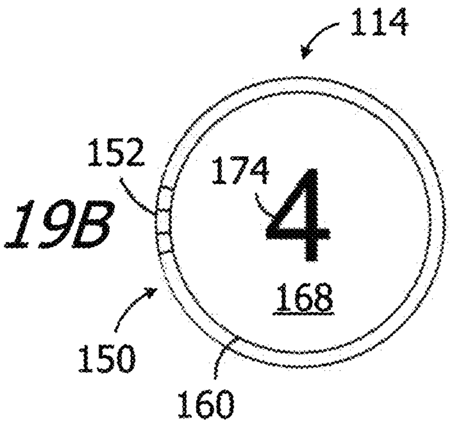
Figure 20A:
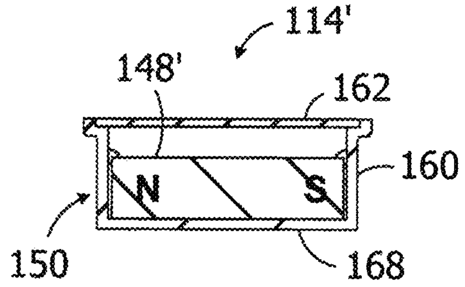
FIGS. 20A and 20B are section and bottom views of a magnet apparatus in accordance with one embodiment of a present invention.
Figure 20B:
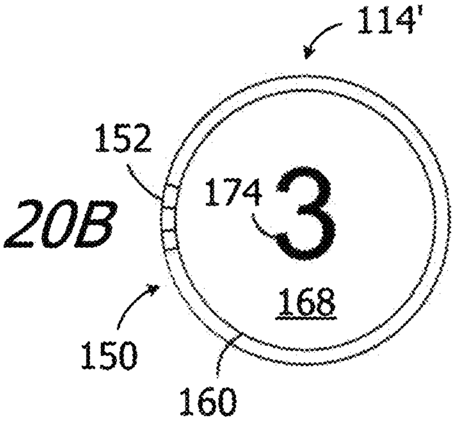
Figure 21A:
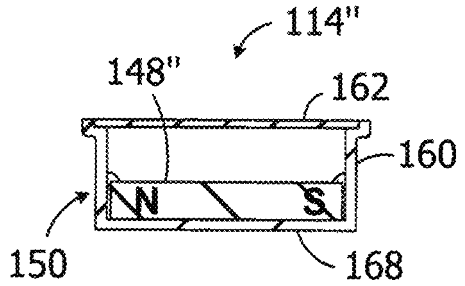
FIGS. 21A and 21B are section and bottom views of a magnet apparatus in accordance with one embodiment of a present invention.
Figure 21B:
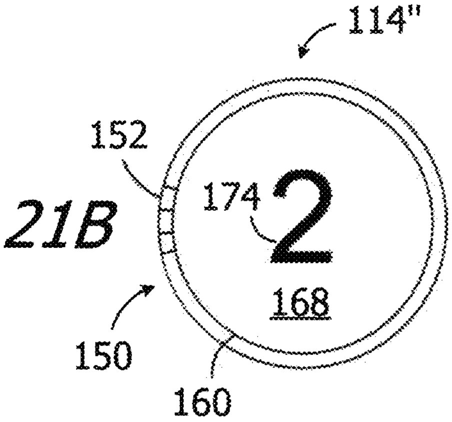
Figure 22A:
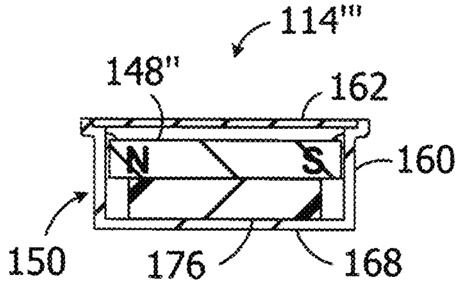
FIGS. 22A and 22B are section and bottom views of a magnet apparatus in accordance with one embodiment of a present invention.
Figure 22B:
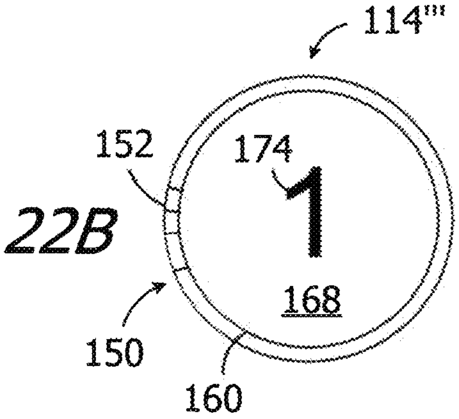

Referring first to FIGS. 19A and 19B, the above-described magnet apparatus 114 may be provided with indicia 174 on the container bottom wall 168 that is representative of relative magnetic strength. The magnet apparatus illustrated in FIGS. 20A-22B are substantially similar to magnet apparatus 114 and similar elements are represented by similar reference numerals. For example, the magnet cases 150 are the same size and shape. The respective magnetic strengths of the magnet apparatus illustrated in FIGS. 20A-22B are, however, different than that of magnet apparatus 114 and are different than those of one another. The exemplary magnet apparatus 114' illustrated in FIGS. 20A-20B includes a diametrically magnetized magnet 148' that, like the magnet 148 of magnet apparatus 114, is in contact with the container bottom wall 168 and the bottom wall includes indicia 174. The magnet 148' in magnet apparatus 114' is, however, smaller than the magnet 148 in magnet apparatus 114. As such, the strength of magnet apparatus 114 is greater than that of magnet apparatus 114'. Similarly, the exemplary magnet apparatus 114" illustrated in FIGS. 21A-21B includes a diametrically magnetized magnet 148" that, like the magnets 148 and 148' of magnet apparatus 114 and 114', is in contact with the container bottom wall 168 and the bottom wall includes indicia 174. The magnet 148" in magnet apparatus 114" is, however, smaller than the magnet 148' in magnet apparatus 114'. As such, the strength of magnet apparatus 114' is greater than that of magnet apparatus 114". Turning to FIGS. 22A and 22B, the magnet apparatus 114" is identical to magnet apparatus 114" but for the fact that the magnet 148" in magnet apparatus 114'" is separated from the container bottom wall 168 by a non-magnetic spacer 176 (e.g., a polyoxymethylene spacer). The distance between the magnet 148" in magnet apparatus 114'" and the implanted cochlear implant magnet will be greater than the distance associated with of the magnet apparatus 114" and, accordingly, the strength of the magnet apparatus 114" is considered to be greater than that of the magnet apparatus 114'".

In other implementations, the variations in magnet apparatus strength may be accomplished through variations in magnet strength. For example, the magnets 148', 148" and 148'" may be the same size as the magnet 148, and occupy the same position within the associated magnet apparatus, but be formed from successively weaker magnetic materials.

The indicia 174 of the magnet apparatus 114-114'" is indicative of relative strength. In the illustrated implementation, numeric indicia is employed with the numbers increasing from weakest to strongest. For example, magnet apparatus 114'" is labeled "1" and magnet apparatus 114 is labeled "4."

Figure 23:
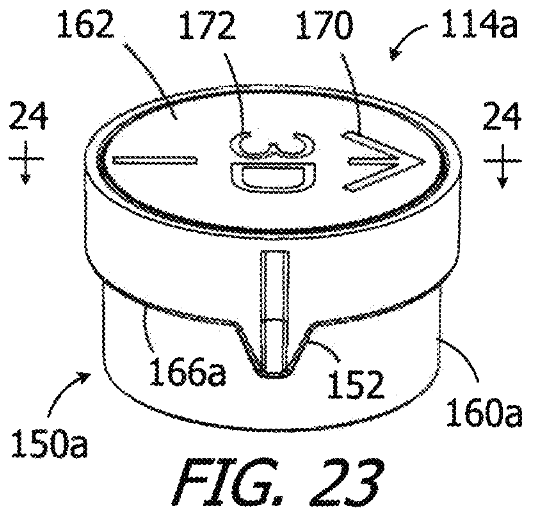
FIG. 23 is a perspective view of a magnet apparatus in accordance with one embodiment of a present invention.
Figure 24:
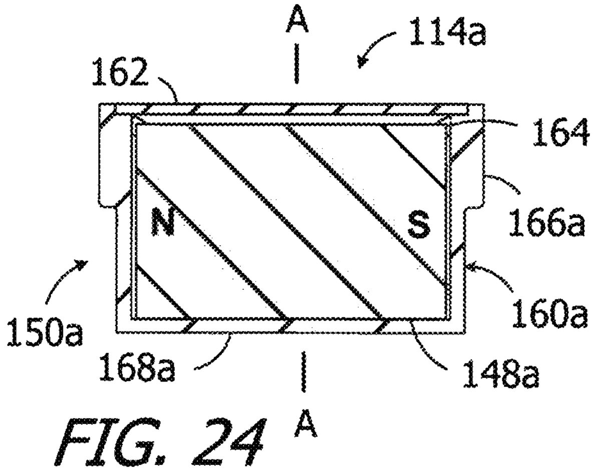
FIG. 24 is a section view taken along line 24-24 in FIG. 23.

Larger magnets (as compared to magnet 148) may be used to create still stronger magnet apparatus. Referring to FIGS. 23 and 24, the exemplary magnet apparatus 114*a* is substantially similar to magnet apparatus 114 and similar elements are represented by similar reference numerals. For example, the magnet apparatus 114*a* includes a diametrically magnetized magnet 148*a* and a magnet case 150*a*. The magnet case 150*a* has container 160*a* that is configured to receive the magnet 148*a*, a cover 162 that prevents removal of the magnet from the magnet case, adhesive 164, and a flange 166*a* at the top end of the container 160*a*. A lock member 152 is located on, and projects outwardly from, the outer surface of the magnet case 150*a*. The magnet 148*a* is, however, larger than magnet 148. Although the diameters of the magnets are the same (e.g., 11 mm), the magnet 148*a* is longer in the axial direction than the magnet 148. Similarly, although the inner and outer diameters of the magnet cases 150 and 150*a* are the same, magnet case 150*a* is longer in the axial direction than magnet case 150 to accommodate the longer magnet 148*a* and, in particular, the container 160*a* is longer than the container 160. The magnet case 150*a* is also sized, shaped and otherwise configured such that the magnet apparatus 114*a* can be placed into the receptacle 116 of housing 102, and the distance between the lock member 152 and the container bottom wall 168*a* is the same as that of the magnet apparatus 114. As such, the magnet apparatus 114*a* may also be fixed in the desired N-S orientation in the manner described above with reference to FIGS. 10-18.

Figure 25:
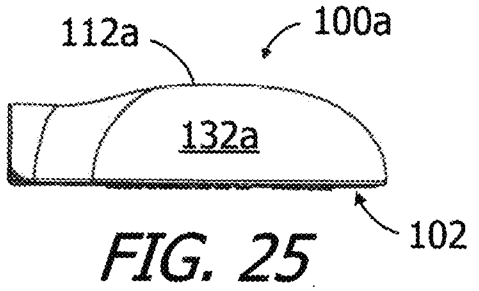
FIG. 25 is a side view of a headpiece in accordance with one embodiment of a present invention.
Figure 26:
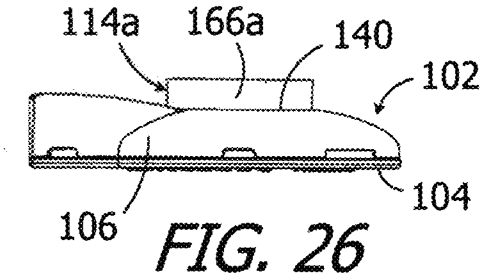
FIG. 26 is a side view of a portion of the headpiece illustrated in FIG. 25.
Figure 27:
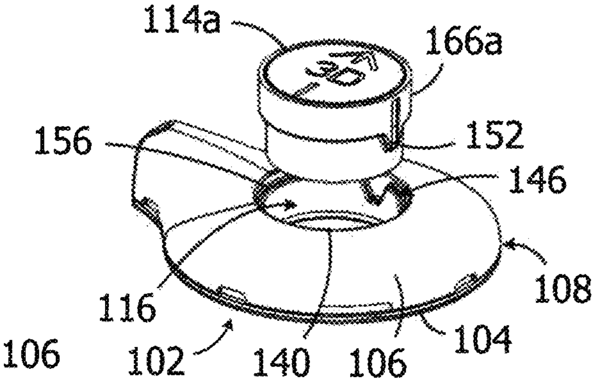
FIG. 27 is an exploded perspective view of a portion of the headpiece illustrated in FIG. 25.

Turning to FIGS. 25-27, the exemplary headpiece 100*a* with magnet apparatus 114*a* is essentially identical to headpiece 100 with magnet apparatus 114, and similar elements are represented by similar reference numerals. The exemplary headpiece 100*a* includes the housing 102 (as well as the components therein), the larger magnet apparatus 114*a*, and a removable cap 112*a* that is configured to accommodate the larger magnet apparatus. When the magnet apparatus 114*a* is fully inserted into the housing receptacle 116, with the respective lock members 146 and 152 engaged (i.e., with the lock member 152 in one of the indentations 158) and the flange 166*a* resting on the base top surface 156, a portion of the flange will extend upwardly beyond the receptacle top end 140 (FIG. 26). The removable cap 112*a* accommodates the larger magnet apparatus 114*a* by way of a bulbous main portion 132*a* that rests on the magnet apparatus when the cap is secured to the housing 102 by way of the latch indentations 136 and latches 138 or other suitable instrumentalities.

Figure 28:
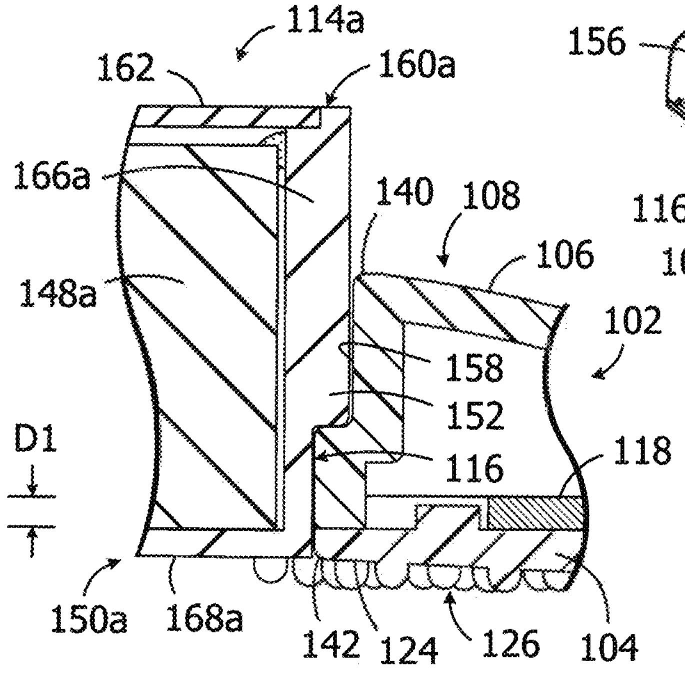
FIG. 28 is a section view of a portion of the headpiece illustrated in FIG. 25.

As is illustrated for example in FIG. 28, the case bottom wall 168*a* of the magnet apparatus 114*a* extends through the housing base member 104 to the receptacle open bottom end 142, and the bottom end of the case 150*a* is aligned with the adjacent portion of the bottom surface 124 of the base member, when the magnet apparatus is fully inserted into the receptacle 116. Such an arrangement reduces the distance between headpiece magnet 148*a* and the implanted cochlear implant magnet (not shown) by a distance D1, as compared to an arrangement where the magnet apparatus rests on the inner surface of the housing base member, and increases the magnetic attraction between the magnets, as is discussed in greater detail above with reference to FIG. 18.

Figure 29:
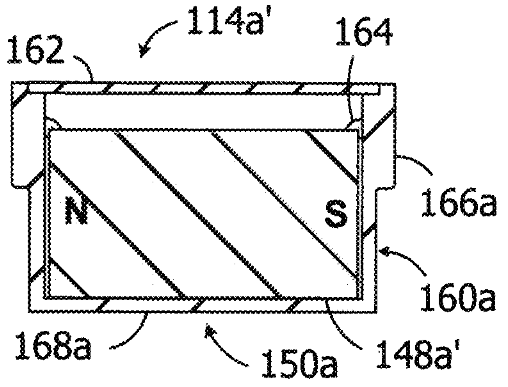
FIG. 29 is a section view of a magnet apparatus in accordance with one embodiment of a present invention.

Here too, the size of a magnet and/or the distance of the magnet from the case bottom wall 168*a* may be varied. For example, and referring to FIG. 29, the exemplary magnet apparatus 114*a'* is essentially identical to magnet apparatus 114*a* but for a smaller diametrically magnetized magnet 148*a'*. The diameters of the exemplary magnets are the same, but the magnet 148*a'* is shorter in the axial direction than the magnet 148. The strength of magnet apparatus 114*a'* is, accordingly, less than that of magnet apparatus 114*a*.

Figure 30:
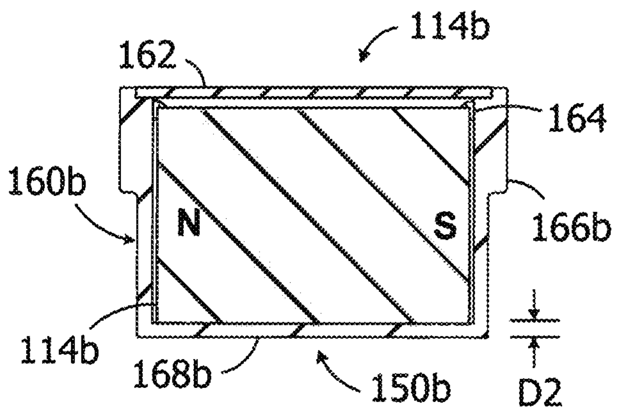
FIG. 30 is a section view of a magnet apparatus in accordance with one embodiment of a present invention.
Figure 31:
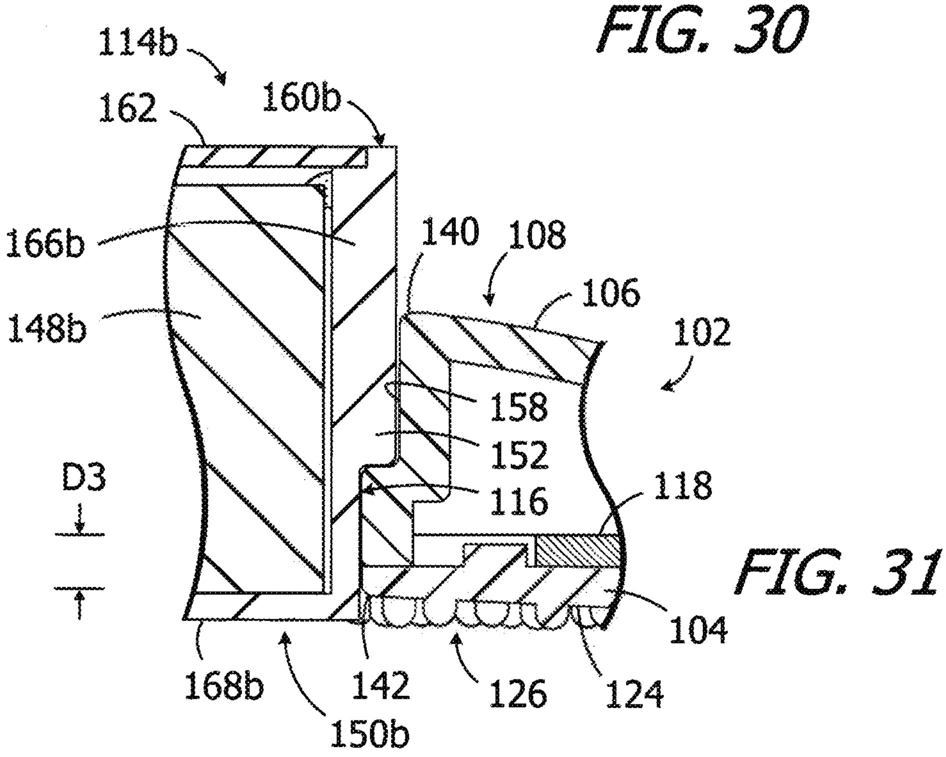
FIG. 31 is a section view of a portion of a headpiece in accordance with one embodiment of a present invention.

The exemplary magnet apparatus 114*b* illustrated in FIGS. 30 and 31, on the other hand, is configured to place the associated magnet closer to the implant magnet than the magnet apparatus 114*a*. The magnet apparatus 114*b* is substantially similar to the magnet apparatus 114*a* and similar elements are represented by similar reference numerals. For example, the magnet apparatus 114*b* includes a diametrically magnetized magnet 148*b* and a magnet case 150*b*. The magnet case 150*b* has container 160*b* that is configured to receive the diametrically magnetized magnet 148*b*, a cover 162 that prevents removal of the magnet from the magnet case, adhesive 164, and a flange 166*b* at the top end of the container 160*b*. A lock member 152 is also provided. The magnet apparatus 114*b* is, however, configured such that the distance between the bottom end of the flange 166*b* and the outer surface of the container bottom wall 168*b* is greater than that of the magnet apparatus 114 by a distance D2. The distance D2 in the illustrated embodiment is slightly less or equal to the length of the protrusions 126 measured from the free ends thereof to the base member 104 (e.g., about 0.5 mm). The additional length of this portion of the magnet case 150*b* results in the magnet apparatus 114*b* extending through and downwardly beyond the adjacent portion of the bottom surface 124 of the base member 104. Such an arrangement decreases the distance between headpiece magnet 148*b* and the implanted cochlear implant magnet (not shown) by a distance D3 (which is the sum of distances D1 and D2), as compared to an arrangement where the magnet apparatus rests on the inner surface of the housing base member, and increases the magnetic attraction between the magnets.

It should also be noted here that the present headpieces may also include magnet apparatus with axially magnetized magnets for use in conjunction with certain cochlear implants such as, for example, cochlear implants that include an axially magnetized implant magnet. More specifically, the housing 102 (as well as the internal components thereof) may be used in conjunction with a magnet apparatus, including an axially magnetized magnet, that is configured to be received within the housing receptacle 116. This facilitates production of a modular headpiece which may be used with cochlear implants that require an axially magnetized headpiece magnet as well as with cochlear implants that require that required a diametrically magnetized headpiece magnet. Although the rotational orientation of an axially magnetized magnet has no effect on the strength of the attraction between the headpiece magnet and the cochlear implant magnet, magnet apparatus with axially magnetized magnets may include the same magnet case that is employed in magnet apparatus with diametrically magnetized (e.g., magnet case 150) in order to simplify the manufacturing, inventory, and distribution processes. Alternatively, otherwise identical magnet cases without the lock member 152 may be provided.

Figure 32:
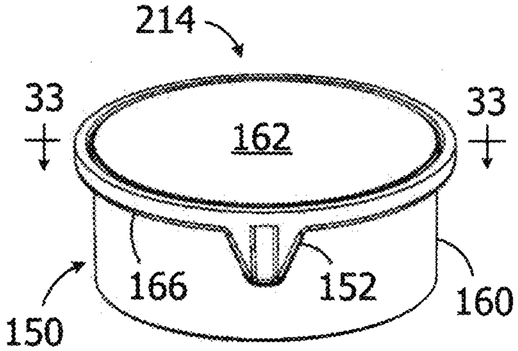
FIG. 32 is a perspective view of a magnet apparatus in accordance with one embodiment of a present invention.
Figure 33:
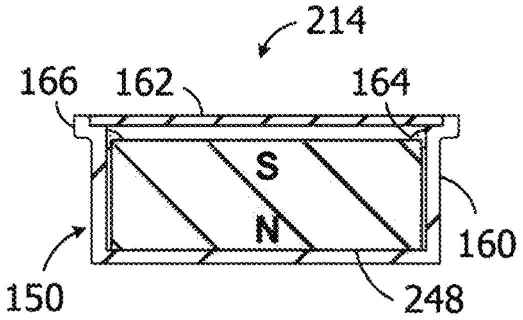
FIG. 33 is a section view taken along line 33-33 in FIG. 32.
Figure 36:
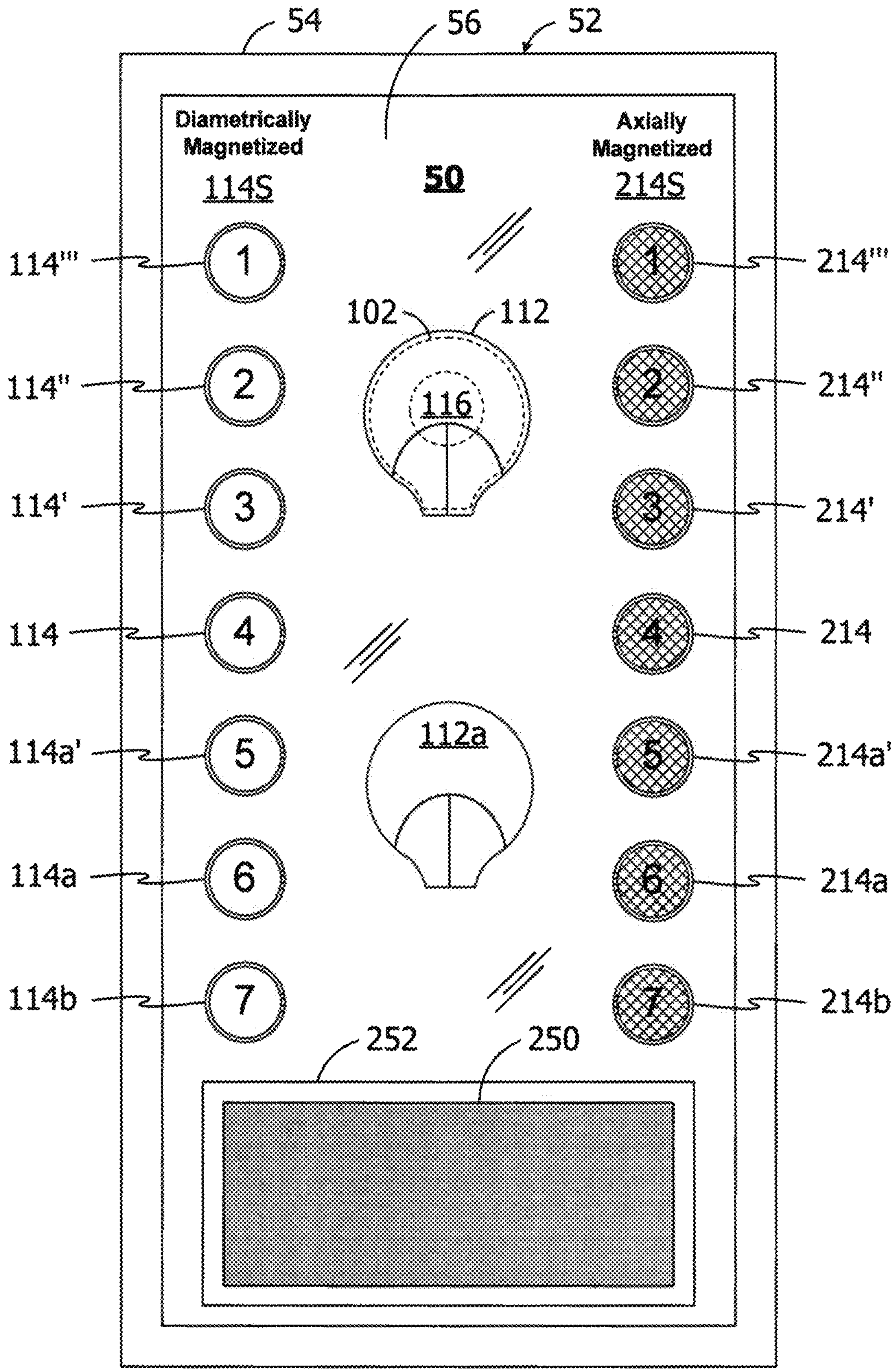
FIG. 36 is a plan view of a kit in accordance with one embodiment of a present invention.

Referring to FIGS. 32 and 33, the exemplary magnet apparatus 214 illustrated therein is substantially similar to the magnet apparatus 114 described above with reference to FIGS. 12 and 13. Here, however, the magnet apparatus 214 includes an axially magnetized magnet 248 in the above-described magnet case 150 and lacks indicia representative N-S direction. Other indicia may be provided in some instances to identify the magnet apparatus 214 as an axially magnetized magnet apparatus. The exemplary magnet apparatus 214 is configured to be received within the housing receptacle 116 in the same manner as the magnet apparatus 114. The strength of the magnet apparatus 214 may be modified in the manner described above with reference to FIGS. 19A-22B. In particular, the magnet apparatus 214', 214" and 214'" (shown in FIG. 36) may, but for the use of an axially magnetized magnet, be configured in the same manner as the magnet apparatus 114', 114" and 114'". As such, the strength of magnet apparatus 214 is greater than that of magnet apparatus 214', the strength of magnet apparatus 214' is greater than that of magnet apparatus 214", and the strength of magnet apparatus 214" is greater than that of magnet apparatus 214'".

Figure 34:
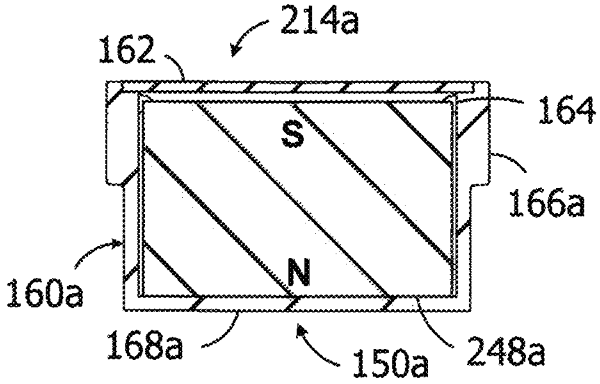
FIG. 34 is a section view of a magnet apparatus in accordance with one embodiment of a present invention.

Turning to FIG. 34, magnet apparatus 214*a* illustrated therein is substantially similar to the magnet apparatus 114*a* described above with reference to FIGS. 23-28. Here, however, the magnet apparatus 214*a* includes an axially magnetized magnet 248*a* in the above-described magnet case 150*a* and lacks indicia representative N-S direction. Other indicia may be provided in some instances to identify the magnet apparatus 214*a* as an axially magnetized magnet apparatus. The exemplary magnet apparatus 214*a* is configured to be received within the housing receptacle 116 in the same manner as the magnet apparatus 114*a*. The strength of the magnet apparatus 214*a* may be modified in the manner described above with reference to FIG. 29, i.e. by reducing the size of the magnet, which results in a magnet apparatus 214*a*' (shown in FIG. 36) with a magnetic strength that is less than that of magnet apparatus 214*a*.

Figure 35:
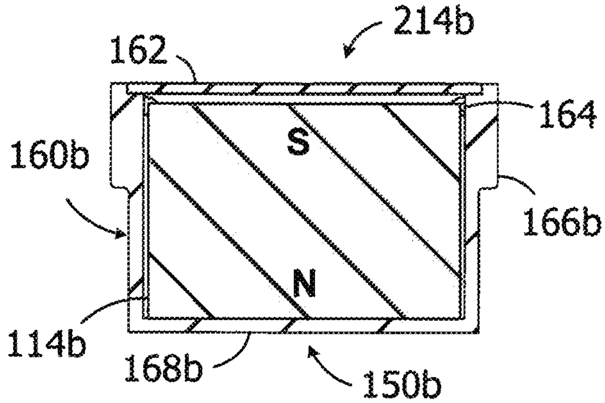
FIG. 35 is a section view of a magnet apparatus in accordance with one embodiment of a present invention.

The exemplary magnet apparatus 214*b* illustrated in FIG. 35 is substantially similar to the magnet apparatus 114*b* described above with reference to FIGS. 30 and 31. Here, however, the magnet apparatus 214*b* includes an axially magnetized magnet 248*b* in the above-described magnet case 150*b* and lacks indicia representative N-S direction. Other indicia may be provided in some instances to identify the magnet apparatus 214*b* as an axially magnetized magnet apparatus. The exemplary magnet apparatus 214*b* is configured to be received within the housing receptacle 116 in the same manner as the magnet apparatus 114*b*.

Magnet apparatus such as those described above may form part of magnet apparatus systems that allow audiologists to select the most appropriate magnet apparatus strength (and magnet apparatus orientation) during the fitting process. As illustrated for example in FIG. 36, the exemplary magnet apparatus system 114S may include the diametrically magnetized magnet apparatus 114'", 114", 114', 114, 114*a*', 114*a* and 114*b* with indicia in the form of numerals 1-7 on the bottom surfaces thereof. The numerals identify in ascending order the relative strengths of the magnet apparatus in the magnet apparatus system 114S. Similarly, the exemplary magnet apparatus system 214S may include the axially magnetized magnet apparatus 214'", 214", 214', 214, 214*a*', 214*a* and 214*b* with indicia in the form of numerals 1-7 on the bottom surfaces thereof. The numerals identify in ascending order the relative strengths of the magnet apparatus in the magnet apparatus system 214S. The bottom surfaces of magnet apparatus in the magnet apparatus system 214S includes other indicia such as color (as shown) to indicate that the magnet apparatus are axially magnetized. The magnet apparatus systems 114S and 214S may also be combined and considered a single magnet apparatus system.

One or both of the exemplary magnet apparatus systems 114S and 214S may be provided as part of a kit 50 to, for example, audiologists for use during the fitting process. Here, the magnet apparatus systems 114S and 214S may be located within the packaging 52, which in the illustrated implementation includes a box or other enclosure 54 with a cover 56, for shipping and storage. The cover 56 may be transparent, as shown, or opaque. The kit 50 may also include a headpiece housing 102, a cap 112 and a cap 112*a*.

The exemplary kit 50 may also be provided with a magnetic viewing device 250 that the clinician, surgeon, MRI technician or other person may use to identify the type of magnet (or magnet apparatus) that is implanted in a patient, as well as the location of magnet (or magnet apparatus). The magnetic viewing device 250 may also be provided separately. As discussed in greater detail below, the magnetic viewing device 250 may be used to display certain aspects of the magnetic field of the implanted magnet(s), and the clinician may use the displayed aspects to identify the magnet type as well as the magnet location.

The exemplary magnetic viewing device 250 may be a sheet of magnetic viewing film. Such a film may, for example, be in the form of a flexible translucent film (e.g., a translucent green film) which is coated with micro-capsules that contain nickel flakes suspended in oil. When placed next to a magnet, the orientation and reflectiveness of the nickel flakes will depend on the direction of the magnetic lines of force. The nickel flakes are reflective and appear bright in those areas of the sheet where the magnetic lines of force are parallel to the surface of the sheet, and appear significantly darker in those area of sheet where the magnetic lines of force are perpendicular to the surface of the sheet. One example of a magnetic viewing film is that sold by K&J Magnetics, Inc. of Pipersville, Pennsylvania under the tradename Magne-View. Various other examples of magnetic viewing film are sold by Hangseng Magnetech Co., Ltd. of Ningbo, China. In some instances, the magnetic viewing device 250 may be sealed within a protective transparent sheet 252.

Figure 37:
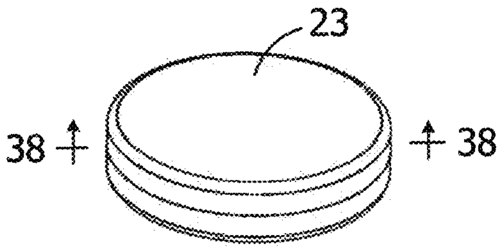
FIG. 37 is a perspective view of an implant magnet within a case.
Figure 38:
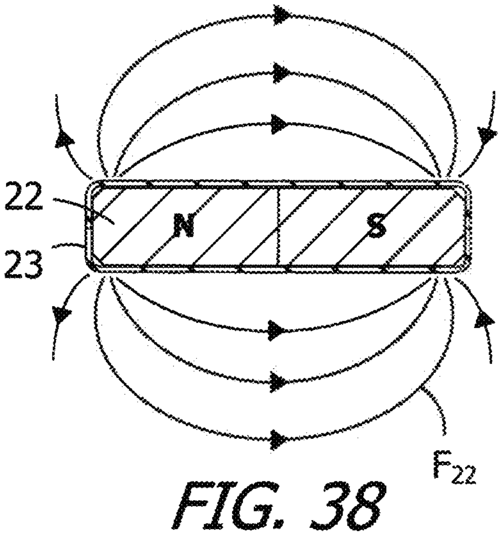
FIG. 38 is a section view taken along line 38-38 in FIG. 37.
Figure 39:
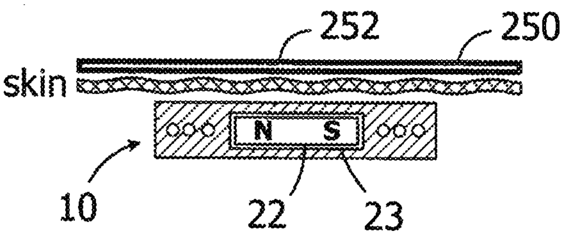
FIG. 39 is a section view showing a method in accordance with one embodiment of a present invention employed in conjunction with the implant magnet illustrated in FIGS. 37 and 38.
Figure 40:
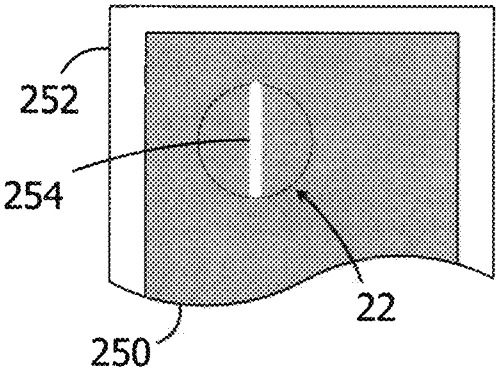
FIG. 40 is a plan view showing one aspect of the method illustrated in FIG. 39.

As illustrated in FIGS. 37 and 38, a diametrically magnetized disk-shaped magnet 22 may be located within a titanium case 23. The magnet 22, which is rotatable relative to the case 23 about an axis A, generates a magnetic field with lines of force $F_{22}$. The magnetic lines of force $F_{22}$ are parallel to the top and bottom surfaces of the magnet 22 at the intersection of the North and South poles. Turning to FIGS. 39 and 40, one exemplary method identifying the magnet within an implanted cochlear implant, such as the above-described cochlear implant 10, involves placing a magnetic viewing device, such as the magnetic viewing device 250 within the protective transparent sheet 252, on the patient's head (i.e., against the patient's skin or hair) over the cochlear implant when the magnet is in a flat state that is parallel (or mostly parallel) to the skin. The location of the magnet 22 is shown with a dashed line, which is not actually present on the magnetic viewing device 250, to aid the discussion. The bright area 254 of the magnetic viewing device 250, which is where the magnetic lines of force are parallel to the surface of the sheet, is a single straight line. Such a single straight line is indicative of a diametrically magnetized disk-shaped magnet (such as magnet 22), and the clinician, surgeon, MRI technician or other person may identify the magnet at issue as a diametrically magnetized disk-shaped magnet based on the presence of a bright area 254 in the form of a straight line. The bright area 254 is also indicative of magnet location.

Figure 41:
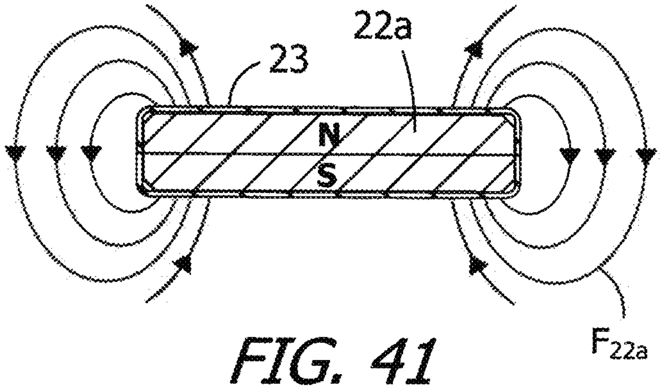
FIG. 41 is a section view of an implant magnet within a case.
Figure 42:
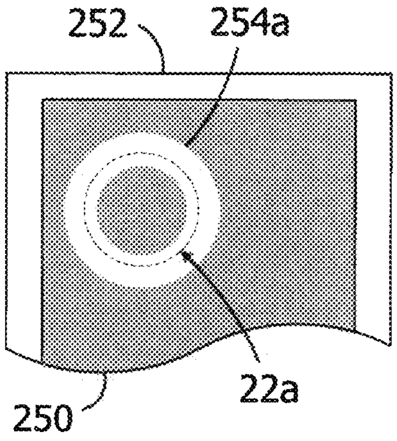
FIG. 42 a plan view showing an aspect of a method in accordance with one embodiment of a present invention employed in conjunction with the implant magnet illustrated in FIG. 41.

The exemplary axially magnetized disk-shaped magnet **22*a* illustrated in FIG. 41 is located within a titanium case 23. The magnet 22*a* generates a magnetic field with lines of force $F_{22a}$. The magnet 22*a* and case 23 may be located under the skin and within a cochlear implant in a manner essentially identical to that illustrated in FIG. 39. Referring to FIG. 42, the magnetic viewing device 250 may be placed on the patient's head over a cochlear implant that includes the magnet 22*a* when the magnet is in a flat state that is parallel (or mostly parallel) to the skin. The location of the magnet 22*a* is shown with a dashed line, which is not actually present on the magnetic viewing device 250, to aid the discussion. The bright area 254*a* of the magnetic viewing device 250, which is where the magnetic lines of force are parallel to the surface of the sheet, is annular in shape. The annular shape is indicative of an axially magnetized disk-shaped magnet (such as magnet 22*a*), and the clinician, surgeon, MRI technician or other person may identify the magnet at issue as an axially magnetized disk-shaped magnet based on the presence of the annular bright area 254*a*. The bright area 254*a*** is also indicative of magnet location.

It should also be noted here that the magnetic viewing device 250 may be used in conjunction with cochlear implant magnets that are not circular. For example, when the magnetic viewing device 250 is placed on the patient's head over a square magnet in a flat state that has a polar orientation that is parallel to the length of the magnet (similar to FIG. 39), the bright area of the magnetic viewing device will be a single straight line. Alternatively, when the magnetic viewing device 250 is placed on the patient's head over a square magnet in a flat state with a polar orientation that is perpendicular to the length of the magnet (similar to FIG. 41), the bright area of the magnetic viewing device will be a square annular shape.

Figure 43:
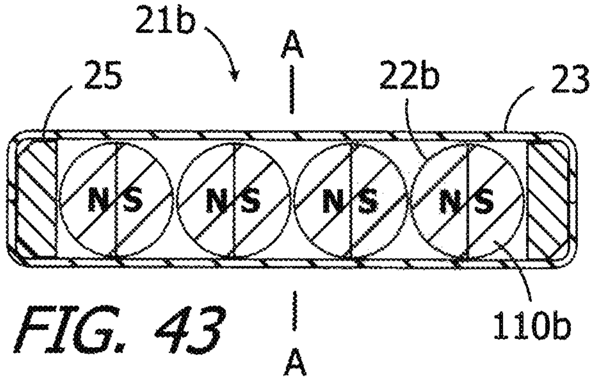
FIG. 43 is a section view of an implant magnet apparatus.
Figure 44:
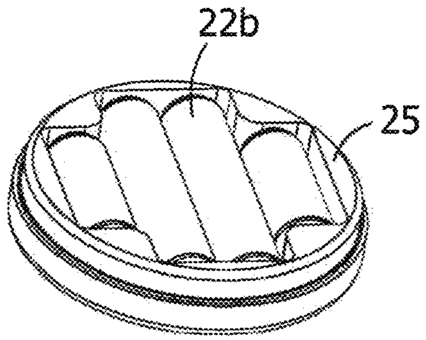
FIG. 44 is a perspective view of a portion of the magnet apparatus illustrated in FIG. 43.

Turning to FIGS. 43 and 44, the exemplary magnet apparatus **21*b* includes a plurality of elongate diametrically magnetized magnets 22*b* that are located in a frame 25. The magnets 22*b* and frame 25 are located within a case 23. The frame 25 is rotatable about the central axis A of the case, and the magnets 22*b* are rotatable about their respective longitudinal axes relative to the frame. Various examples of magnet apparatus with a plurality of rotating elongate magnets within a rotating frame are disclosed in U.S. Pat. No. 10,463,849. One simplified computer generated possible representation of the magnetic field generated by the magnets 22*b*, with lines of force $F_{22b}$, is illustrated in FIG. 44**A.

Figure 44A:
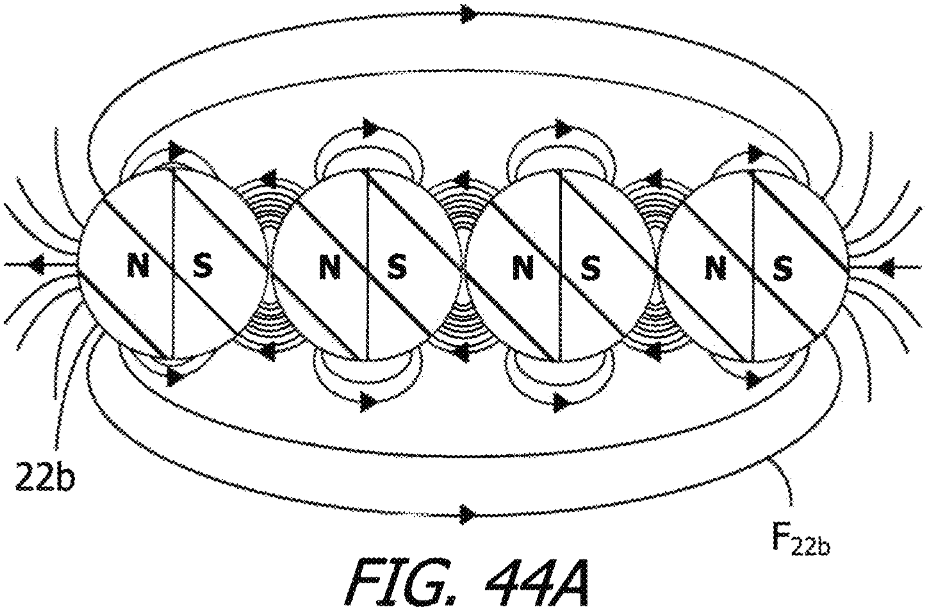
FIG. 44A is a section view of a portion of the implant magnet apparatus illustrated in FIGS. 43 and 44.
Figure 45:
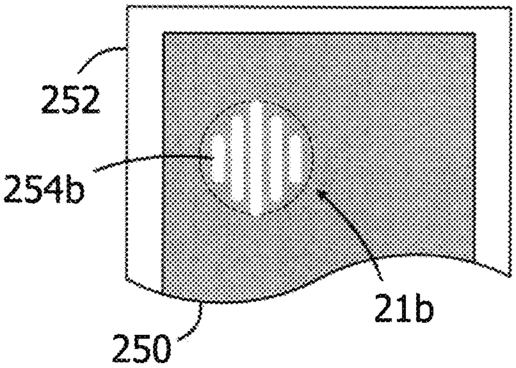
FIG. 45 a plan view showing an aspect of a method in accordance with one embodiment of a present invention employed in conjunction with the implant magnet apparatus illustrated in FIGS. 43 and 44.

Referring to FIG. 45, the magnetic viewing device 250 may be placed on the patient's head over a cochlear implant that includes the magnet apparatus **21*b*. The location of the magnet apparatus 21*b* is shown with a dashed line, which is not actually present on the magnetic viewing device 250, to aid the discussion. Assuming the presence of the magnetic field illustrated in FIG. 44A, the bright area 254*b* of the magnetic viewing device 250, which is where the magnetic lines of force are parallel to the surface of the sheet, is in the form of a plurality of spaced straight lines that correspond to the higher intensity portions of the magnetic field. The straight lines are indicative of a plurality of side-by-side diametrically magnetized elongate magnets (such as magnets 22*b*), and the clinician, surgeon, MRI technician or other person may identify the magnet apparatus as a magnet apparatus that includes a plurality of side-by-side diametrically magnetized elongate magnets by the bright area 254*b* with a plurality of side-by-side straight lines. The bright area 254*b*** is also indicative of magnet location.

It should also be noted here that the magnetic viewing device 250, or another magnetic viewing device, may be used to identify information about the magnet in one of the above-described headpiece magnet apparatus (or any other headpiece magnet) in those instances where the clinician, surgeon, MRI technician or other person desires to do so.

The exemplary headpiece 100 (or **100*a*) may be used in ICS systems such as, for example, the exemplary ICS system 60 illustrated in FIG. 46. The system 60 includes the cochlear implant 10, a headpiece 100 (or 100*a*), and a sound processor 200**, such as a body worn sound processor or a behind-the-ear sound processor.

The exemplary sound processor 300 is a body worn sound processor that includes a housing 302 in which and/or on which various components are supported. Such components may include, but are not limited to, sound processor circuitry 304, a headpiece port 306 that may be connected to the headpiece 100 by a cable 308, an auxiliary device port 310 for an auxiliary device such as a mobile phone or a music player, a control panel 312, one or more microphones 314, and a power supply receptacle 316 for a removable battery or other removable power supply 318 (e.g., rechargeable and disposable batteries or other electrochemical cells). The sound processor circuitry 304 converts electrical signals from the microphone 314 into stimulation data.

During use, the magnet of an above-described headpiece magnet apparatus (e.g., magnet 148 of magnet apparatus 114) will be attracted to the implant magnet 22, thereby aligning the headpiece antenna 120 with the implant antenna 20. The stimulation data and, in many instances power, is supplied to the headpiece 100, which transcutaneously transmits the stimulation data, and in many instances power, to the cochlear implant 10 by way of a wireless link between the antennas. In at least some implementations, the cable 308 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques.

Figure 47:
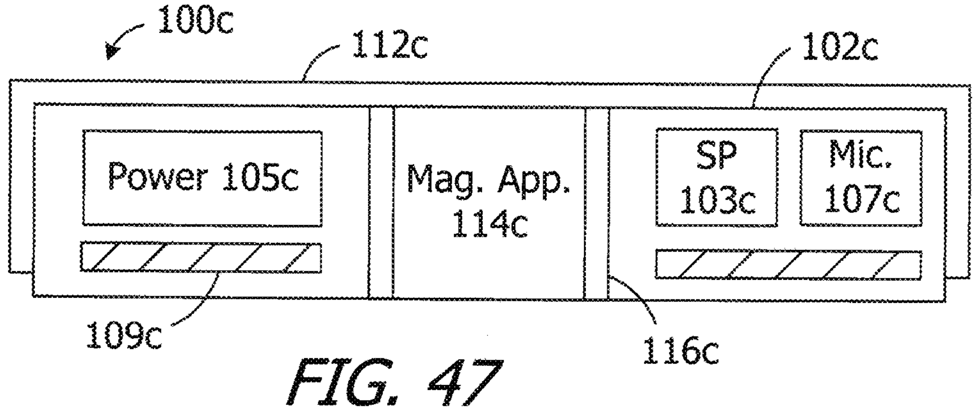
FIG. 47 is a block diagram of a headpiece in accordance with one embodiment of a present invention.

It should be noted that the present inventions have application in ICS systems which are configured such that all of the external components (e.g., the battery, the microphone, the sound processor, and the antenna) are carried within a single headpiece, and there is no BTE or body worn sound processor connected to the headpiece by a cable. One example of such a headpiece is generally represented by reference numeral 100*c* in FIG. 47. The exemplary headpiece 100*c* may include a housing 102*c* with an internal volume that contains a sound processor 103*c*, a power supply 105*c*, a microphone 107*c* and an annular antenna 109*c*. The exemplary headpiece 100*c* also includes a magnet apparatus 114*c*, a receptacle 116*c*, and a removable cap 112*c* that may be secured to the housing. The magnet apparatus 114*c* and receptacle 116*c* may have configurations that are the same as, or that are similar to, the configurations of any of the magnet apparatus and receptacles described above. For example, the receptacle 116*c*, which extends completely though the associated housing in a manner similar to receptacle 116 (FIGS. 6 and 8), has open top and bottom ends. The removable cap 112*c* holds the magnet apparatus 114*c* in a manner similar to cap 112 (FIGS. 14 and 15). It should be noted, however, that due to the additional components such as the power supply 105*c* and sound processor 103*c*, the headpiece 100*c* may be heavier than headpieces intended for use with a separate sound processor. As such, the magnet apparatus 114*c* and receptacle 116*c* may also be larger than the other magnet apparatus and receptacles described above to accommodate the larger diametrically magnetized and axially magnetized magnets that may be required by the heavier headpiece 100*c*.

Although the inventions disclosed herein have been described in terms of the preferred embodiments above, numerous modifications and/or additions to the above-described preferred embodiments would be readily apparent to one skilled in the art. By way of example, but not limitation, although the exemplary headpieces 100 and 100*a* described above do not include microphones, one or more microphones may be provided within the housing 102 in other implementations. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant headpiece for use with a cochlear implant, the cochlear implant headpiece comprising:

a housing including an exterior, a top wall, a bottom wall configured to face the cochlear implant and a receptacle that extends from the top wall to the bottom wall, that defines an open top end that extends to the housing exterior, an open bottom end that extends to the housing exterior and a central axis, and that includes a receptacle lock member;

a magnet apparatus defining a bottom portion, a bottom end, a top portion, and a top end and including a magnet and a magnet apparatus lock member;

a removable cap configured to be mounted on the housing top wall and to cover the open top end of the magnet receptacle and the top end of the magnet apparatus when mounted on the housing; and a headpiece antenna on or within the housing;

wherein the magnet apparatus can be inserted into the receptacle through the open top end of the receptacle and removed from the receptacle through the open top end of the receptacle and, when fully inserted into the receptacle, the bottom portion of the magnet apparatus extends through the open bottom end of the receptacle and the magnet apparatus bottom end is located downwardly beyond the open bottom end of the receptacle and at least a portion of the magnet is located within the receptacle; and the fully inserted magnet apparatus will be fixed in one of a plurality of rotational orientations around the central axis.

2. The cochlear implant headpiece claimed in claim 1, wherein the magnet apparatus is not rotatable relative to the receptacle when fully inserted into the receptacle.

3. The cochlear implant headpiece claimed in claim 1, wherein the magnet apparatus includes a case and a cover and the magnet is located within the case.

4. The cochlear implant headpiece claimed in claim 1, wherein the magnet apparatus includes a radially extending flange;

the receptacle lock member defines a top surface; and the radially extending flange abuts the top surface of the receptacle lock member when the magnet apparatus is fully inserted into the receptacle.

5. The cochlear implant headpiece as claimed in claim 1, wherein the receptacle lock member includes a plurality of slots; and the magnet apparatus lock member comprises a projection.

6. The cochlear implant headpiece claimed in claim 1, wherein the housing defines a ring-like portion and includes a circuitry within the ring-like portion.

7. The cochlear implant headpiece claimed in claim 6, wherein the headpiece antenna is located within the substantially ring-like portion.

8. The cochlear implant headpiece claimed in claim 1, wherein the housing top wall defines a housing top surface; and the magnet apparatus top end is flush with an adjacent portion of the housing top surface when the magnet apparatus is fully inserted into the receptacle.

9. The cochlear implant headpiece claimed in claim 1, wherein the housing top wall defines a housing top surface; and the magnet apparatus top end is located outwardly beyond an adjacent portion of the housing top surface when the magnet apparatus is fully inserted into the receptacle.

10. The cochlear implant headpiece as claimed in claim 1, wherein the headpiece magnet comprises a diametrically magnetized magnet.

11. The cochlear implant headpiece claimed in claim 1, wherein the magnet comprises an axially magnetized magnet.

12. The cochlear implant headpiece claimed in claim 1, further comprising:

a sound processor within the housing.

13. A cochlear stimulation system, comprising:

the cochlear implant headpiece claimed in claim 1; and a cochlear implant including a cochlear implant magnet and a cochlear implant antenna.

14. A cochlear stimulation system, comprising:

the cochlear implant headpiece claimed in claim 1; and a sound processor including a sound processor housing, and sound processor circuitry carried within the sound processor housing and operably connected to the headpiece antenna.

15. The cochlear stimulation system claimed in claim 14, further comprising:

a cochlear implant including a cochlear implant magnet and a cochlear implant antenna.

16. The cochlear implant headpiece claimed in claim 1, wherein the housing includes a plurality of protrusions that extend downwardly from the bottom wall and that each define a protrusion length; and when the magnet apparatus is fully inserted into the receptacle, the magnet apparatus bottom end is located downwardly beyond the open bottom end by a distance that is less than or equal to the length of the protrusions.

* * * * *